United States Patent
Yuzhakov et al.

(10) Patent No.: US 7,060,192 B2
(45) Date of Patent: Jun. 13, 2006

(54) METHODS OF FABRICATING PHYSIOLOGICAL SAMPLE COLLECTION DEVICES

(75) Inventors: Vadim V Yuzhakov, San Jose, CA (US); Devin V. McAllister, San Jose, CA (US); Lorin Olson, Scotts Valley, CA (US); Koon-wah Leong, Sunnyvale, CA (US); Maria Teodorczyk, San Jose, CA (US); Ernest Kiser, Los Altos, CA (US)

(73) Assignee: LifeScan, Inc., Milpitas, CA (US)

( * ) Notice: Subject to any disclaimer, the term of this patent is extended or adjusted under 35 U.S.C. 154(b) by 375 days.

(21) Appl. No.: 10/143,127

(22) Filed: May 9, 2002

(65) Prior Publication Data

US 2003/0212346 A1 Nov. 13, 2003

(51) Int. Cl.
*B32B 31/00* (2006.01)
*C03C 25/68* (2006.01)

(52) U.S. Cl. .......................................... 216/11; 600/347
(58) Field of Classification Search .................... 216/2, 216/10, 11; 600/576, 583, 584; 604/272; 606/181
See application file for complete search history.

(56) References Cited

U.S. PATENT DOCUMENTS

| | | | |
|---|---|---|---|
| 3,964,482 A | 6/1976 | Gerstel et al. | |
| 4,627,445 A | 12/1986 | Garcia et al. | |
| 4,731,726 A | 3/1988 | Allen, III | |
| 4,966,159 A | 10/1990 | Maganias | |
| 5,151,231 A * | 9/1992 | Lambert et al. | 264/108 |
| 5,161,532 A | 11/1992 | Joseph | |
| 5,364,374 A | 11/1994 | Morrison et al. | |
| 5,409,664 A * | 4/1995 | Allen | 422/56 |
| 5,457,041 A | 10/1995 | Ginaven et al. | |
| 5,582,184 A | 12/1996 | Erickson et al. | |
| 5,591,139 A | 1/1997 | Lin et al. | |
| 5,682,233 A | 10/1997 | Brinda | |
| 5,697,901 A | 12/1997 | Eriksson | |
| 5,746,217 A | 5/1998 | Erickson et al. | |
| 5,762,770 A * | 6/1998 | Pritchard et al. | 204/403.14 |
| 5,801,057 A * | 9/1998 | Smart et al. | 436/68 |
| 5,820,570 A | 10/1998 | Erickson et al. | |
| 5,823,973 A | 10/1998 | Racchini et al. | |
| 5,855,801 A * | 1/1999 | Lin et al. | 216/2 |
| 5,879,310 A | 3/1999 | Sopp et al. | |
| 5,879,326 A | 3/1999 | Godshall et al. | |
| 5,928,207 A | 7/1999 | Pisano et al. | |

(Continued)

FOREIGN PATENT DOCUMENTS

EP 1174078 1/2002

(Continued)

OTHER PUBLICATIONS

Inverness Medical Ltd et al, "Analyte Measurement" PCT Patent Application 96.72742/001, Unpublished.

*Primary Examiner*—Parviz Hassanzadeh
*Assistant Examiner*—Roberts Culbert
(74) *Attorney, Agent, or Firm*—Kagan Binder PLLC

(57) ABSTRACT

Methods of fabricating devices for collecting a sample of physiological and for measuring a characteristic, e.g., an analyte concentration, of the sampled physiological sample. The devices are in the form of a test strip which include a biosensor and at least one skin-piercing element which is a planar extension of a portion of the biosensor. The fabrication methods provide various or forming the test strip and the skin-piercing element.

22 Claims, 13 Drawing Sheets

U.S. PATENT DOCUMENTS

| | | |
|---|---|---|
| 5,961,451 A | 10/1999 | Reber et al. |
| 6,080,116 A | 6/2000 | Erickson et al. |
| 6,091,975 A | 7/2000 | Daddona et al. |
| 6,099,484 A | 8/2000 | Douglas et al. |
| 6,120,464 A | 9/2000 | Racchini et al. |
| 6,152,889 A | 11/2000 | Sopp et al. |
| 6,155,992 A | 12/2000 | Henning et al. |
| 6,203,504 B1 | 3/2001 | Latterell et al. |
| 6,219,574 B1 | 4/2001 | Cormier et al. |
| 6,230,051 B1 | 5/2001 | Cormier et al. |
| 6,334,856 B1 | 1/2002 | Allen et al. |
| 6,364,890 B1 | 4/2002 | Lum et al. |
| 6,375,627 B1 | 4/2002 | Mauze et al. |
| 6,379,324 B1 | 4/2002 | Gartstein et al. |
| 6,472,220 B1 | 10/2002 | Simons et al. |
| 6,612,111 B1 * | 9/2003 | Hodges et al. ............... 60/583 |
| 2001/0027277 A1 | 10/2001 | Klitmose |
| 2002/0004196 A1 | 1/2002 | Whitson |
| 2002/0133129 A1 * | 9/2002 | Arias et al. ............... 604/272 |
| 2002/0137998 A1 * | 9/2002 | Smart et al. ............... 600/347 |
| 2003/0171699 A1 * | 9/2003 | Brenneman ............... 600/584 |
| 2004/0176732 A1 * | 9/2004 | Frazier et al. ............... 604/345 |

FOREIGN PATENT DOCUMENTS

| | | |
|---|---|---|
| WO | WO9742888 | 11/1997 |
| WO | WO9800193 | 1/1998 |
| WO | WO9834541 | 8/1998 |
| WO | WO9964580 | 12/1999 |
| WO | WO0035530 | 6/2000 |
| WO | WO0074763 A2 | 12/2000 |
| WO | WO0074764 A1 | 12/2000 |
| WO | WO0074765 A1 | 12/2000 |
| WO | WO0074766 A1 | 12/2000 |
| WO | WO0172220 | 10/2001 |
| WO | WO0172225 | 10/2001 |

* cited by examiner

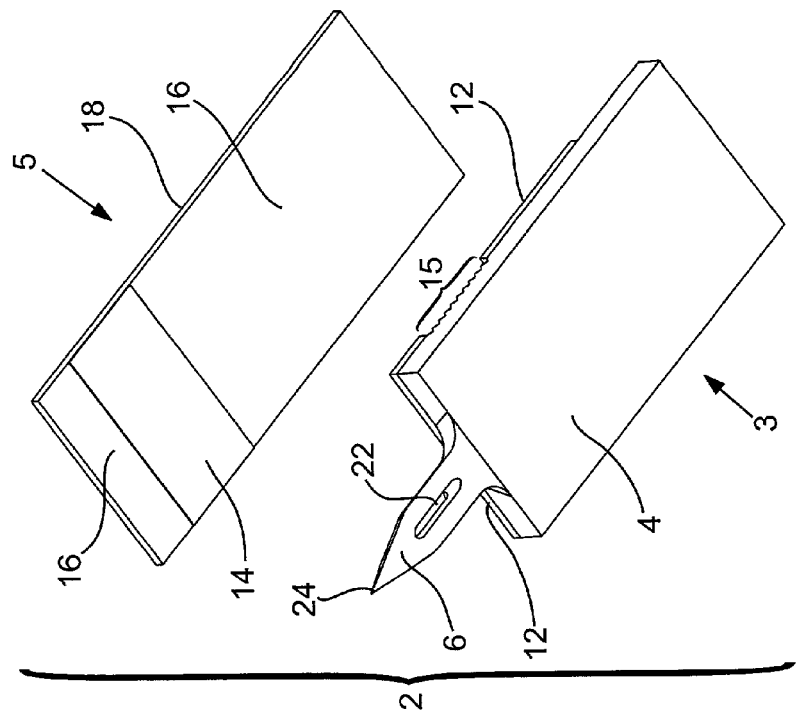
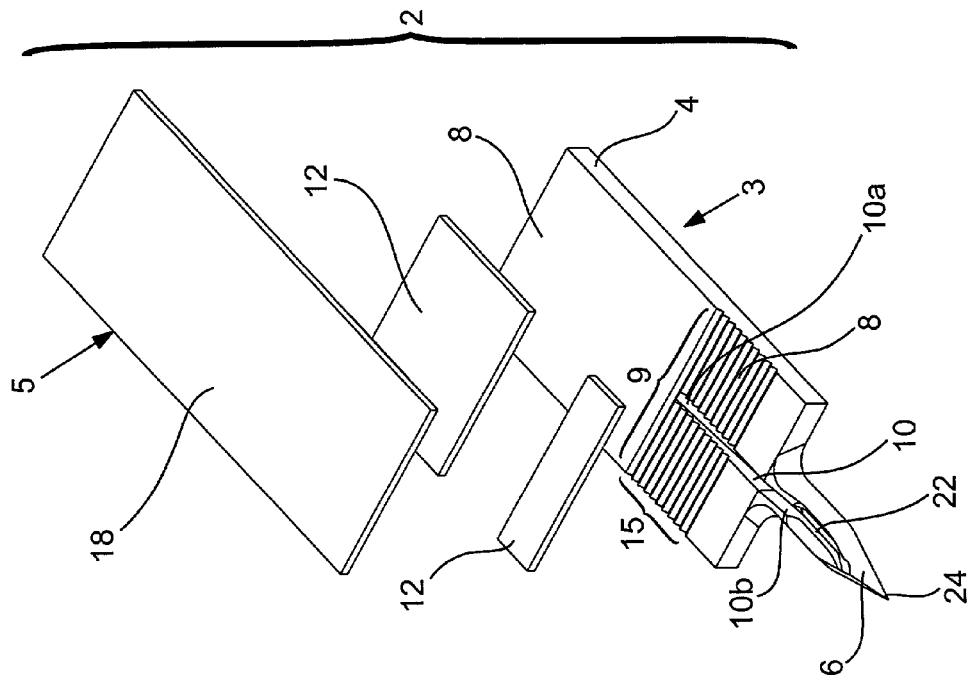

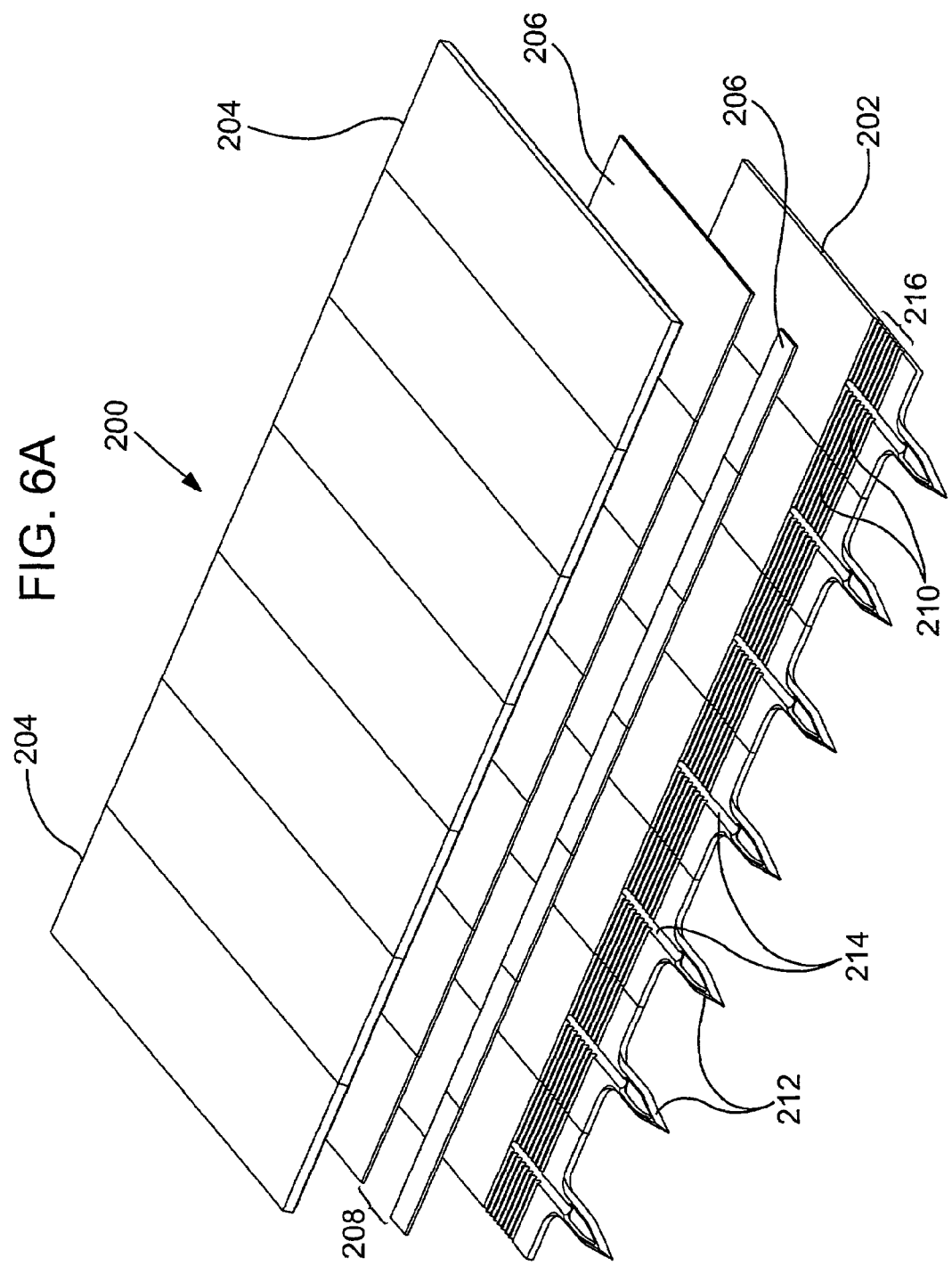

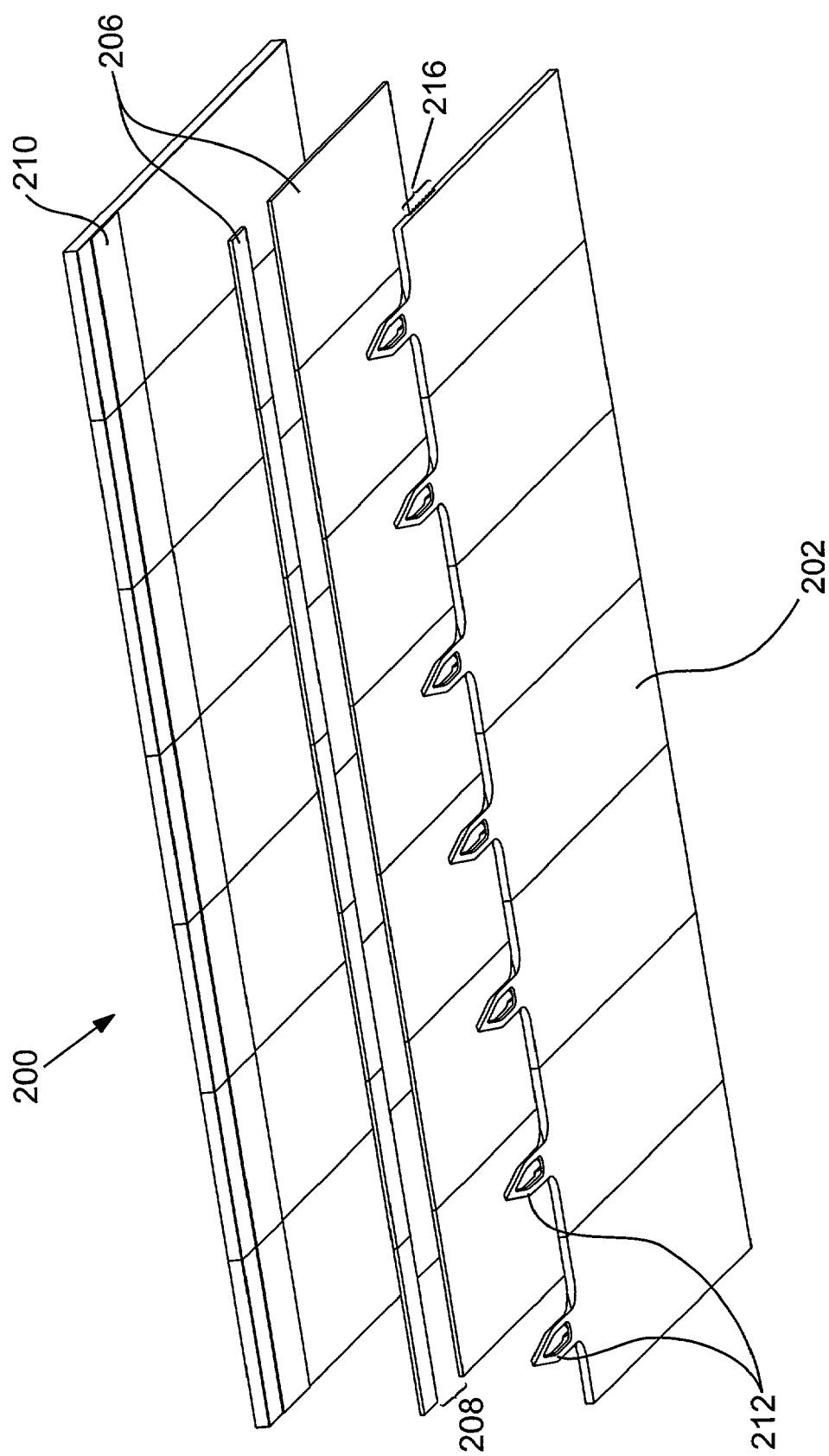

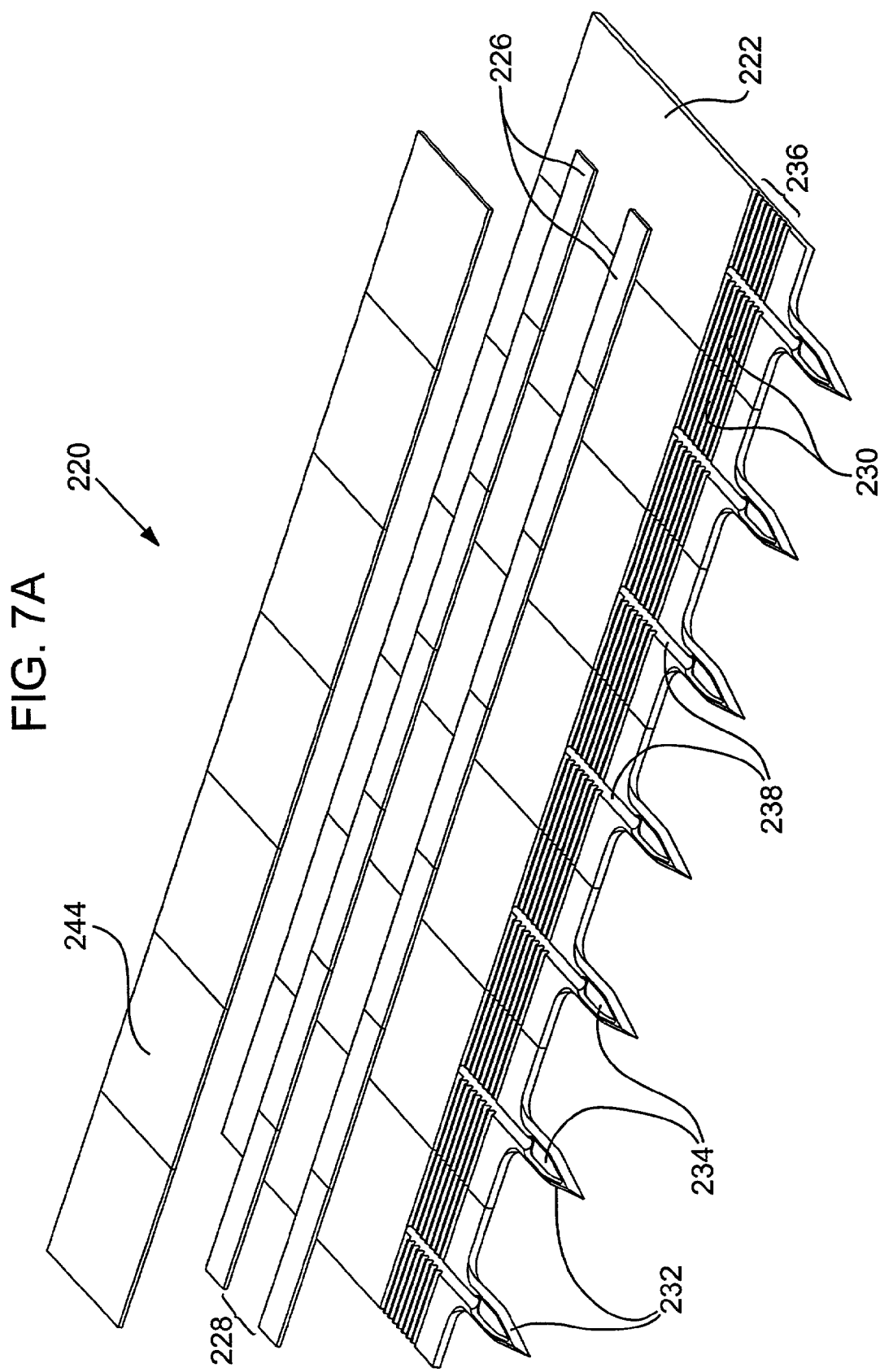

METHODS OF FABRICATING PHYSIOLOGICAL SAMPLE COLLECTION DEVICES

FIELD OF THE INVENTION

The field of this invention is the collection of physiological samples and the determination of analyte concentrations therein.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like. In response to this growing importance of analyte concentration determination, a variety of analyte concentration determination protocols and devices for both clinical and home testing have been developed.

In determining the concentration of an analyte in a physiological sample, a physiological sample must first be obtained. Obtaining the sample often involves cumbersome and complicated devices which may not be easy to use or may be costly to manufacture. Furthermore, the procedure for obtaining the sample may be painful. For example, pain is often associated with the size of the needle used to obtain the physiological sample and the depth to which the needle is inserted. Depending on the analyte and the type of test employed, a relatively large, single needle or the like is often used to extract the requisite amount of sample.

The analyte concentration determination process may also involve a multitude of steps. First, a sample is accessed by use of a skin-piercing mechanism, e.g., a needle or lancet, which accessing may also involve the use of a sample collection mechanism, e.g., a capillary tube. Next, the sample must then be transferred to a testing device, e.g., a test strip or the like, and then oftentimes the test strip is then transferred to a measuring device such as a meter. Thus, the steps of accessing the sample, collecting the sample, transferring the sample to a biosensor, and measuring the analyte concentration in the sample are often performed as separate, consecutive steps with various device and instrumentation.

Because of these disadvantages, it is not uncommon for patients who require frequent monitoring of an analyte to simply become non-compliant in monitoring themselves. With diabetics, for example, the failure to measure their glucose level on a prescribed basis results in a lack of information necessary to properly control the level of glucose. Uncontrolled glucose levels can be very dangerous and even life threatening.

Attempts have been made to combine a lancing-type device with various other components involved in the analyte concentration determination procedure in order to simplify the assay process. For example, U.S. Pat. No. 6,099,484 discloses a sampling device which includes a single needle associated with a spring mechanism, a capillary tube associated with a pusher, and a test strip. An analyzer may also be mounted in the device for analyzing the sample. Accordingly, the single needle is displaced toward the skin surface by un-cocking a spring and then retracting it by another spring. A pusher is then displaced to push the capillary tube in communication with a sample and the pusher is then released and the fluid is transferred to a test strip.

U.S. Pat. No. 5,820,570 discloses an apparatus which includes a base having a hollow needle and a cover having a membrane, whereby the base and cover are connected together at a hinge point. When in a closed position, the needle is in communication with the membrane and fluid can be drawn up through the needle and placed on the membrane of the cover.

There are certain drawbacks associated with each of the above devices and techniques. For example, the devices disclosed in the aforementioned patents are complex, thus decreasing ease-of-use and increasing manufacturing costs. Furthermore, as described, a single needle design may be associated with increased pain because the single needle must be large enough to extract the requisite sample size. Still further, in regards to the '484 patent, the steps of activating and retracting a needle and then activating and retracting a capillary tube adds still more user interaction and decreases ease-of-use.

As such, there is continued interest in the development of new devices and methods for use in the determination of analyte concentrations in a physiological sample. Of particular interest would be the development of integrated devices, and methods of use thereof, that are efficient, involve minimal pain, are simple to use and which may be used with various analyte concentration determination systems.

SUMMARY OF THE INVENTION

Devices, systems and methods are provided for piercing the skin, accessing and collecting physiological sample therein, and measuring a characteristic of the physiological sample. The subject devices include at least one microneedle or skin-piercing element integral with a test strip. More specifically, the subject test strips include a biosensor wherein the at least one skin-piercing element is structurally integral with the biosensor.

Each skin-piercing element has a space-defining configuration therein which, upon insertion into the skin, creates a space or volume within the pierced tissue. This space serves as a reservoir or pooling area within which bodily fluid is caused to pool while the skin-piercing element is in situ. A capillary channel or fluid pathway extending from the open space to within the test strip transfers fluid present pooled within the pooling area to the biosensor. In certain embodiments, the space-defining configuration is a recess within a surface of the skin-piercing element. Such a recess may have a concave configuration. In other embodiments, the space-defining configuration is an opening which extends transverse to a dimension of the skin-piercing element and occupies a substantial portion of a width or diameter dimension as well as a substantial portion of a length dimension of the microneedle.

In one embodiment of the subject test strip devices, the biosensor is an electrochemical biosensor having an electrochemical cell having two spaced-apart electrodes. Each skin-piercing element or structure is provided as a parallel or planar extension of one of the electrodes, wherein the skin-piercing element and such electrode are preferably fabricated as a single, unitary piece or structure and are made of the same material.

In another embodiment of the test strip device, the biosensor is a photometric or colorimetric biosensor having a planar substrate defining a photometric matrix area covered by a photometric membrane, collectively configured for receiving a sample to be tested. With a photometric biosensor embodiment, each skin-piercing element or structure is provided as a planar extension of the substrate, wherein the skin-piercing element and such substrate are preferably fabricated as a single, unitary piece or structure and are made of the same material.

The extending skin-piercing element and the associated electrode (in electrochemical biosensors) or substrate (in photometric biosensors) define at least one pathway, wherein the proximal end of the at least one pathway resides within the electrode or substrate portion of the unitary piece and the distal end of the at least one pathway resides within the skin-piercing element or structure. At least a portion of the distal end of the at least one fluid pathway is open to the outside environment. Further, the distal end of the pathway is in fluid communication with the space-defining area of the skin-piercing element. The distal end of such pathway either extends into at least a portion of the space-defining area or terminates at the space-defining area. As such, the fluid pathway provides a capillary channel through which the fluid within the pooling volume defined by the skin-piercing element may be extracted and transferred to the biosensor portion of the test strip device for testing.

The subject systems include one or more subject test strip devices and a meter for receiving a subject test strip and for determining a characteristic of the sampled fluid, e.g., the concentration of at least one analyte in the sample, collected by within the test strip's biosensor. Moreover, such a meter may also provide means for activating and manipulating the test strip wherein the skin-piercing structure is caused to pierce the skin. Additionally, the meter may provide means for storing one or more subject test strips, or a cartridge containing a plurality of such test strips.

Also provided are methods for using the subject devices, as well as kits that include the subject devices and/or systems for use in practicing the subject methods. The subject devices, systems and methods are particularly suited for collecting physiological sample and determining analyte concentrations therein and, more particularly, glucose concentrations in blood, blood fractions or interstitial fluid.

The present invention further includes methods for fabricating the subject test strip devices, in which a microneedle or skin-piercing element is fabricated as an integral part of a biosensor having a test strip configuration. Such devices have wholly integrated functions including accessing the physiological fluid within the skin, extracting such fluid, transferring the fluid to a measurement area and providing the components necessary for the measurement of analyte concentration in the sample. In addition to fabricating wholly integrated test strip devices, the subject fabrication methods are ideal for the fabrication of such devices which have functionally and structurally complex components, such as the microneedles mentioned above. For example, microneedles having intricate shapes or designs, multiple dimensions, small sizes and/or very sharp tips are producible with great repeatability with the subject fabrication methods. The subject methods are also versatile in that they can be used to fabricate biosensors having electrochemical or photometric configurations with certain variations in the fabrication processes. The subject fabrication methods maybe used to fabricate individual test strip devices or a plurality of such test strip devices on a web, film or sheet of suitable material.

These and other objects, advantages, and features of the invention will become apparent to those persons skilled in the art upon reading the details of the methods and systems of the present invention which are more fully described below.

BRIEF DESCRIPTIONS OF THE DRAWINGS

FIG. 1A is an exploded top view of an embodiment of an electrochemical test strip device of the present invention. FIG. 1B is a partially exploded bottom view of the electrochemical test strip device of FIG. 1A. FIG. 1C is a perspective view of the assembled electrochemical test strip device of FIGS. 1A and 1B.

FIG. 6A is an exploded top view of a web of electrochemical test strip devices fabricated according to the methods of the present invention.

FIG. 6B is an exploded bottom view of the web of FIG. 6A.

FIG. 7A is an exploded top view of a web of the photometric/colorimetric test strip devices fabricated according to the methods of the present invention.

DETAILED DESCRIPTION OF THE INVENTION

Figure 1C:
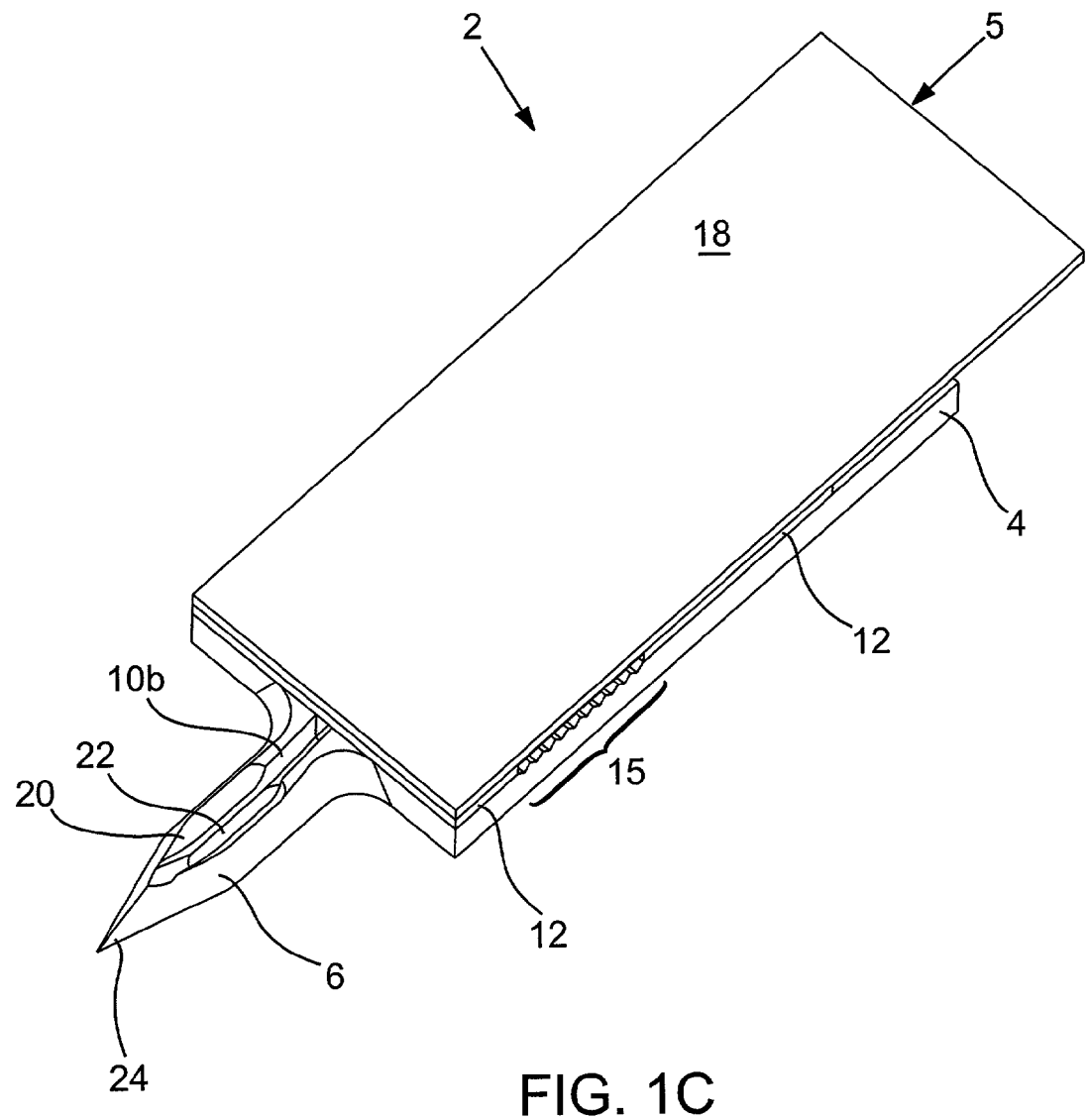

Before the present invention is described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. Thus, for example, reference to "a test strip" includes a plurality of such test strips and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in detail. In further describing the present invention, various embodiments of the subject devices, including test strip devices having biosensors having either an electrochemical or a colorimetric/photometric configuration, will be described first followed by a detailed description of various microneedle configurations which are usable with either type of biosensor configuration. The subject systems which include a meter for use with the subject devices methods of using the subject test strip devices and systems will then be described followed by a description of the methods of fabricating the subject test strip devices. Finally, a brief description is provided of the subject kits, which kits include the subject devices and systems for use in practicing the subject methods.

In the following description, the present invention will be described in the context of analyte concentration measurement applications; however, such is not intended to be limiting and those skilled in the art will appreciate that the subject devices, systems and methods are useful in the measurement of other physical and chemical characteristics of biological substances, e.g., blood coagulation time, blood cholesterol level, etc.

Test Strip Devices

As summarized above, the subject test strip devices include a biosensor and at least one skin-piercing element or microneedle which is structurally integral with the biosensor. The subject biosensor may have an electrochemical configuration, as illustrated in FIGS. 1A, 1B, 1C and FIG. 3 or a colorimetric or photometric (used interchangeably herein), as illustrated in FIGS. 2A and 2B and FIGS. 4A and 4B. Likewise, the subject skin-piercing elements make take on various configurations, wherein a first exemplary embodiment is illustrated in FIGS. 1A, 1B, 1C and 3 and a second exemplary embodiment is illustrated in FIGS. 2A, 2B, 4A and 4B.

In any embodiment, the subject test strip devices and biosensors are useful in the determination of a wide variety of different analyte concentrations, where representative analytes include, but are not limited to, glucose, cholesterol, lactate, alcohol, and the like. In many embodiments, the subject test strips are used to determine the glucose concentration in a physiological sample, e.g., interstitial fluid, blood, blood fractions, constituents thereof, and the like.

Electrochemical Test Strips

Referring now to FIGS. 1A, 1B, 1C and 3, wherein like reference numbers refer to like elements, two electrochemical test strip devices 2 and 100, respectively, of the present invention are illustrated. Test strips 2 and 100 have identical electrochemical biosensor configurations which are herein collectively described, however, their respective skin-piercing elements or microneedles 6 and 102, respectively, have different configurations. In each test strip device 2 and 100, the biosensor is defined by an electrochemical cell generally having two spaced-apart and opposing electrodes 3 and 5, respectively referred to herein as bottom electrode 3 and top electrode 5. At least the surfaces of electrodes 3 and 5 facing each other are comprised of a conductive layer 8 and 16, respectively, such as a metal.

In certain embodiments of the subject electrochemical biosensors, the electrodes are generally configured in the form of elongated rectangular strips but may be of any appropriate shape or configuration. Typically, the length of the electrodes ranges from about 0.5 to 4.5 cm and usually from about 1.0 to 2.8 cm. The width of the electrodes ranges from about 0.07 to 0.8 cm, usually from about 0.20 to 0.60 cm, and more usually from about 0.1 to 0.3 cm. The conductive layers and their associated substrate typically have a combined thickness ranging from about 100 to 500 µm and usually from about 125 to 250 µm.

The entire electrode may be made of the metal or made up of a substrate or backing 4 and 18, respectively on the facing surfaces of which the metal layer 8 and 16, respectively, is provided. In a particular embodiment, substrates 4 and 18 are made of a Mylar plastic film. The thickness of the inert backing material typically ranges from about 25 to 500 µm and usually from about 50 to 400 µm, while the thickness of the metal layer typically ranges from about 10 to 100 nm and usually from about 10 to 50 nm.

As mentioned above, electrodes 3 and 5 generally face each other and are separated by only a short distance, such that the spacing between the electrodes is extremely narrow. This minimal spacing is a result of the presence of a spacer layer 12 positioned or sandwiched between electrodes 3 and 5. The thickness of spacer layer 12 may range from 10 to 750 µm and is often less than or equal to 500 µm, and usually ranges from about 25 to 175 µm. Spacer layer 12 preferably has double-sided adhesive to hold electrodes 3 and 5 together.

In certain embodiments, spacer layer 12 is configured or cut so as to provide a reaction zone or area 9, where in many embodiments the volume of the reaction area or zone 9 typically has a volume in the range from about 0.01 to 10 µL, usually from about 0.1 to 1.0 µL and more usually from about 0.05 to 1.0 µL. However, the reaction area may include other areas of test strip 2 and 100 or be elsewhere all together, such as in a fluid pathway, described below in more detail, or the like. Spacer layer 12 may define any appropriately shaped reaction area 9, e.g., circular, square, triangular, rectangular or irregular shaped reaction areas, and may further include side inlet and outlet vents or ports.

Regardless of where reaction zone 9 is located, in many embodiments, a redox reagent system or composition 14 is present within reaction zone 9, where reagent system 14 is selected to interact with targeted components in the fluid sample during an assay of the sample. Redox reagent system 14 is deposited on the conductive layer 16 of top electrode 5 wherein, when in a completely assembled form (shown in FIG. 1C), redox reagent system 14 resides within reaction zone 9. With such a configuration, bottom electrode 3 serves as a counter/reference electrode and top electrode 5 serves as the working electrode of the electrochemical cell. However, in other embodiments, depending on the voltage sequence applied to the cell, the role of the electrodes can be reversed such that bottom electrode 3 serves as a working electrode and top electrode 5 serves as a counter/reference electrode. In case of a double pulse voltage waveform, each electrode acts as a counter/reference and working electrode once during the analyte concentration measurement.

Reagent systems of interest typically include an enzyme and a redox active component (mediator). The redox component of the reagent composition, when present, is made up of one or more redox agents. A variety of different redox agents, i.e., mediators, is known in the art and includes: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. In many embodiments, the redox active component of particular interest is ferricyanide, and the like. The enzyme of choice may vary depending on the analyte concentration which is to be measured. For example, suitable enzymes for the assay of glucose in whole blood include glucose oxidase or dehydrogenase (NAD or PQQ based). Suitable enzymes for the assay of cholesterol in whole blood include cholesterol oxidase and esterase.

Other reagents that may be present in the reaction area include buffering agents (e.g., citraconate, citrate, malic, maleic, phosphate, "Good" buffers and the like); divalent cations (e.g., calcium chloride, and magnesium chloride); surfactants (e.g., Triton, Macol, Tetronic, Silwet, Zonyl, and Pluronic); and stabilizing agents (e.g., albumin, sucrose, trehalose, mannitol and lactose).

Examples of electrochemical biosensors suitable for use with the subject invention include those described in copending U.S. application Ser. Nos. 09/333,793; 09/497,304; 09/497,269; 09/736,788 and 09/746,116, the disclosures of which are herein incorporated by reference.

Colorimetric/Photometric Test Strips

Referring now to FIGS. 2A, 2B, 4A and 4B, wherein like reference numbers refer to like elements, two photometric/colorimetric test strip devices 80 and 120, respectively, of the present invention are illustrated. Test strips devices 80 and 120 have different photometric/colorimetric biosensor configurations and their respective skin-piercing elements or microneedles 86 and 122, respectively, have different configurations. More specifically, a portion of test strip device 80 is made of an inert material while the corresponding portion of test strip device 120 is made of a metal material.

Figure 2A:
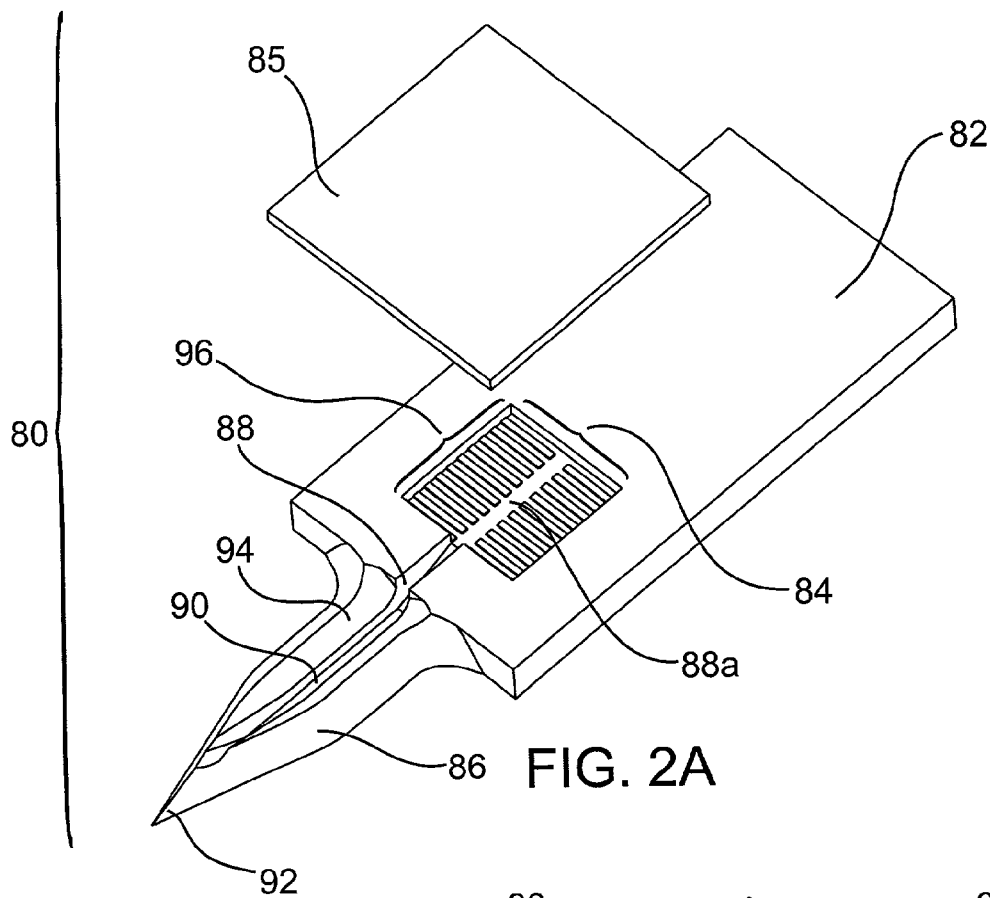
FIG. 2A is an exploded view of an embodiment of a colorimetric or photometric test strip device of the present invention.
Figure 2B:
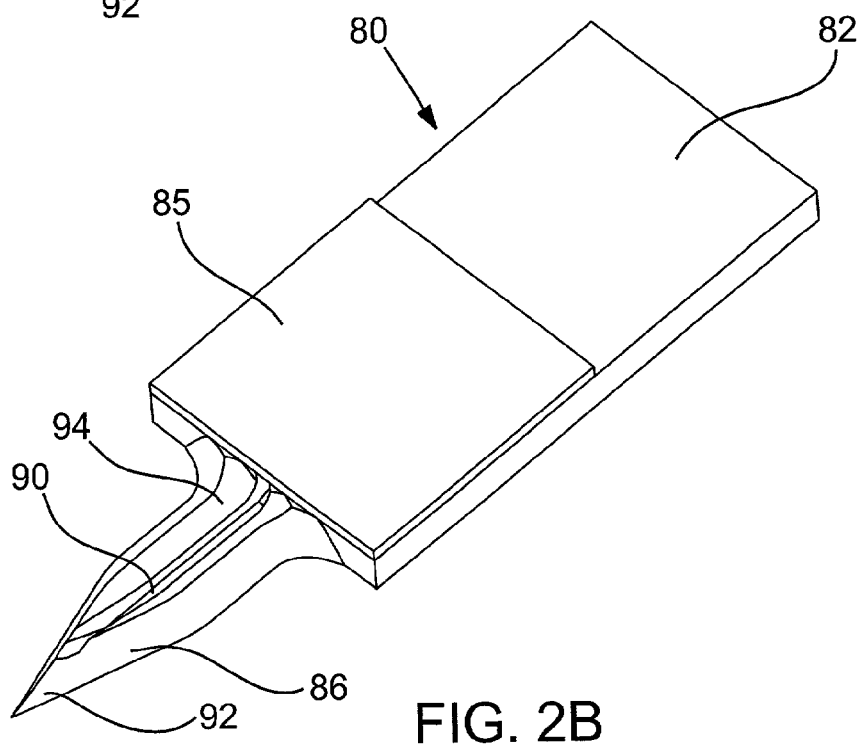
FIG. 2B is a perspective view of the assembled colorimetric/photometric test strip device of FIG. 2A

In test strip device 80 of FIGS. 2A and 2B, the colorimetric or photometric (herein used interchangeably) biosensor is generally made up of at least the following components: a support element or substrate 82 made of an inert material, a matrix 84 for receiving a sample, a reagent composition (not shown as a structural component) within matrix 84 that typically includes one or more members of an analyte oxidation signal producing system, an air venting port (not shown) and a top transparent layer 85 which covers at least matrix 84. In other embodiments, top layer 85 may be a membrane containing a reagent composition impregnated therein while the matrix 84 may or may not contain reagent composition The inert material of support substrate 82 provides a physical structure to enable test strip 80 to be inserted into a meter without undue bending or kinking. Substrate 82, and thus test strip 80, is typically in the form of a substantially rectangular or square-like strip. Typically, the length of the substrate 82 is from about 1 to 1000 mm, usually from about 10 to 100 mm and more usually about 20 to 60 mm. Typically, the width of substrate 82 is from about 1 to 100 mm, usually from about 1 to 10 mm and more usually from about 5 to 7 mm. Typically, the height or thickness of substrate 82 is from about 0.01 to 1 mm, usually from about 0.1 to 1 mm and more usually from about 0.1 to 0.2 mm.

Matrix 84 defines an inert area, preferably a recessed area, formed within a surface of substrate 82 wherein all four sides of matrix 84 are bordered by substrate 82. Matrix 84 provides a deposition area for the sampled physiological sample and for the various members of the signal producing system, described infra, as well as for the light absorbing or chromogenic product produced by the signal producing system, i.e., the indicator, as well as provides a location for the detection of the light-absorbing product produced by the indicator of the signal producing system. In such an embodiment, top layer 85 is transparent so that the color intensity of the chromogenic product resulting from the reaction between the target analyte and the signal producing system can be measured. Transparent layer 85 may, for example, be made of clear thin polyester. This approach, in which the reagent is loaded into matrix 84 and the biosensor is covered with a transparent film 85, is useful in color generation systems that use an enzyme independent of oxygen, such as NAD-, or PQQ-based glucose dehydrogenase.

In yet another embodiment, top layer 85 is one that is permissive of aqueous fluid flow and is sufficiently porous, i.e., provides sufficient void space, for the chemical reactions of the signal producing system to take place. In principle, the nature of porous membrane 85 is critical to the subject test strips in that it should support an aqueous fluid flow both lateral and across the membrane thickness. Ideally, the membrane pore structure would not support red blood cell flow to the surface of the membrane being interrogated, i.e., the color intensity of which is a subject of the measurement correlated to analyte concentration. As such, the dimensions and porosity of test strip 80 may vary greatly, where matrix 84 may or may not have pores and/or a porosity gradient, e.g. with larger pores near or at the sample application region and smaller pores at the detection region. Materials from which matrix membrane 85 may be fabricated vary, include polymers, e.g. polysulfone, polyamides, cellulose or absorbent paper, and the like, where the material may or may not be functionalized to provide for covalent or non-covalent attachment of the various members of the signal producing system.

Figure 4A:
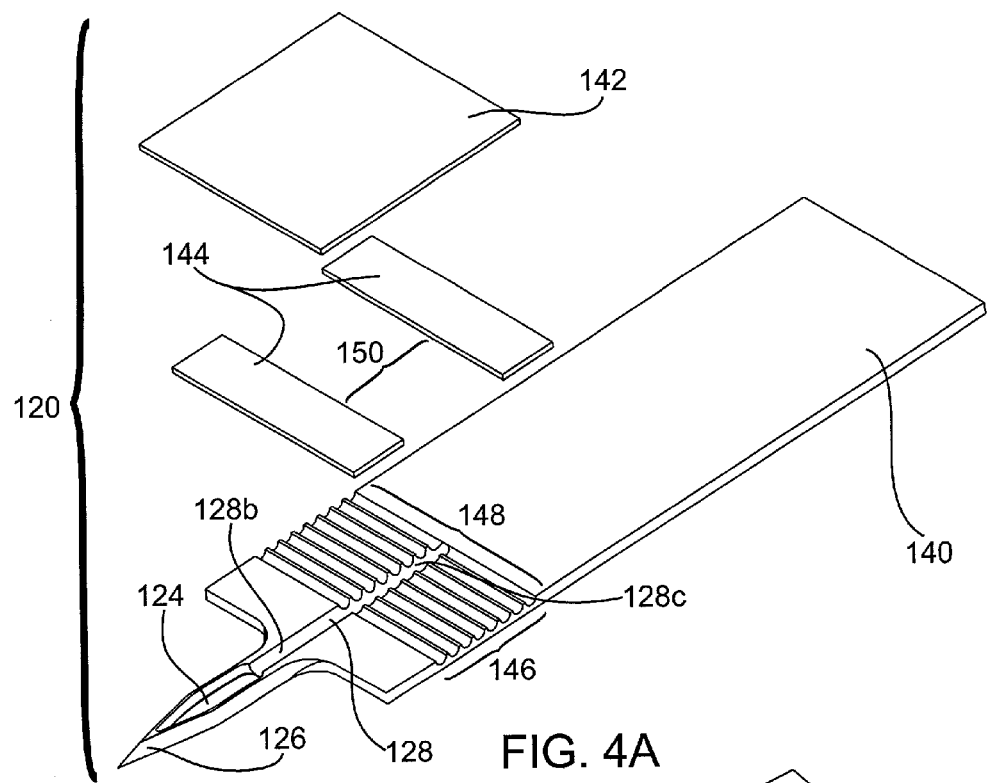
FIG. 4A is an exploded view of another embodiment of a colorimetric or photometric test strip device of the present invention having the skin-piercing element of FIG. 3.
Figure 4B:
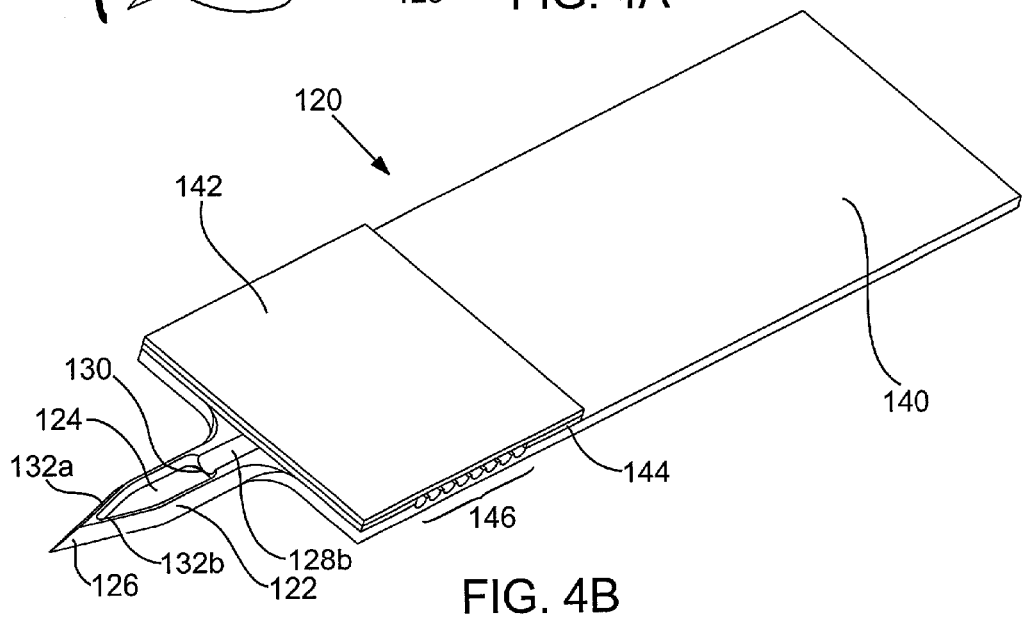
FIG. 4B is a perspective view of the assembled calorimetric/photometric test strip device of FIG. 4A.

While test strip device 120 of FIGS. 4A and 4B has a substrate 140 having a size and shape similar to substrate 82, has a membrane 142 which has a configuration similar to transparent layer 85 and employs the same signal producing system as the test strip device of FIGS. 2A and 2B, there are certain notable differences between the two test strip devices. First, substrate 140 is made of a metal material rather than an inert material. Additionally, matrix 148 is not recessed within substrate 140 and extends across the complete width of substrate 140. Further, test strip 120 has a double-sided adhesive layer 144 situated between substrate 140 and membrane 142. Double-sided adhesive layer 144 has a cut-out portion 150 which corresponds to the area covered by matrix 148 and defines a deposition area as described above with respect to matrix 84. The double-sided adhesive layer 144 holds membrane 142 attached to substrate 140.

A number of different matrices have been developed for use in various analyte detection assays, which matrices may differ in terms of materials, dimensions and the like, where representative matrices usable with the photometric/colorimetric test strip devices of the present invention include, but are not limited to, those described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

The one or more members of the signal producing system produce a detectable product in response to the presence of analyte, which detectable product can be used to derive the amount of analyte present in the assayed sample. In the subject test strips, the one or more members of the signal producing system are associated, e.g., covalently or non-covalently attached to, at least a portion of (i.e., the detection region) the matrix, and in many embodiments to substantially all of the matrix. The signal producing system is an analyte oxidation signal producing system. By analyte oxidation signal producing system is meant that in generating the detectable signal from which the analyte concentration in the sample is derived, the analyte is oxidized by a suitable enzyme to produce an oxidized form of the analyte and a corresponding or proportional amount of hydrogen peroxide. The hydrogen peroxide is then employed, in turn, to generate the detectable product from one or more indicator compounds, where the amount of detectable product generated by the signal measuring system, i.e. the signal, is then related to the amount of analyte in the initial sample. As such, the analyte oxidation signal producing systems present in the subject test strips are also correctly characterized as hydrogen peroxide based signal producing systems.

As indicated above, the hydrogen peroxide based signal producing systems include an enzyme that oxidizes the analyte and produces a corresponding amount of hydrogen peroxide, where by corresponding amount is meant that the amount of hydrogen peroxide that is produced is proportional to the amount of analyte present in the sample. The specific nature of this first enzyme necessarily depends on the nature of the analyte being assayed but is generally an oxidase or dehydrogenase. As such, the first enzyme may be: glucose oxidase (where the analyte is glucose), or glucose dehydrogenase either using NAD or PQQ as cofactor; cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those skilled in the art and may also be employed. In those preferred embodiments where the reagent test strip is designed for the detection of glucose concentration, the first enzyme is glucose oxidase. The glucose oxidase may be obtained from any convenient source, e.g. a naturally occurring source such as *Aspergillus niger* or Penicillum, or recombinantly produced.

The second enzyme of the signal producing system is an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See, e.g., Y. Ci, F. Wang; Analytica Chimica Acta, 233 (1990), 299–302.

The indicator compound or compounds, e.g., substrates, are ones that are either formed or decomposed by the hydrogen peroxide in the presence of the peroxidase to produce an indicator dye that absorbs light in a predetermined wavelength range. Preferably the indicator dye absorbs strongly at a wavelength different from that at which the sample or the testing reagent absorbs strongly. The oxidized form of the indicator may be a colored, faintly-colored, or colorless final product that evidences a change in color of the testing side of the membrane. That is to say, the testing reagent can indicate the presence of glucose in a sample by a colored area being bleached or, alternatively, by a colorless area developing color.

Indicator compounds that are useful in the present invention include both one- and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and 3-methyl-2-benzothiazolinonehydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments of calorimetric test strips, signal producing systems that produce a fluorescent detectable product (or detectable non-fluorescent substance, e.g. in a fluorescent background) may be employed, such as those described in Kiyoshi Zaitsu, Yosuke Ohkura, New fluorogenic substrates for Horseradish Peroxidase: rapid and sensitive assay for hydrogen peroxide and the Peroxidase, Analytical Biochemistry (1980) 109, 109–113. Examples of such calorimetric reagent test strips suitable for use with the subject invention include those described in U.S. Pat. Nos. 5,563,042; 5,753,452; 5,789,255, herein incorporated by reference.

Skin-Piercing Elements/Microneedles

Referring to test strips 2 and 80 of FIGS. 1 and 2, respectively, as well as to test strips 100 and 120 of FIGS. 3 and 4, respectively, the various configurations of skin-piercing element/microneedles of the present invention will now be discussed in greater detail. As discussed above, test strip device 100 includes an electrochemical biosensor configuration similar to that of test strip 2 of FIG. 1 while test strip device 120 includes a colorimetric/photometric biosensor configuration similar to that of test strip 80 of FIG. 2; however, the test strip devices 100 and 120 of FIGS. 3 and 4, respectively, differ from those of FIGS. 1 and 2 in that they have a different microneedle configuration. In both embodiments, the microneedles extend from a substrate of the respective test strip. Specifically, in the electrochemical test strip device embodiments of FIGS. 1 and 3, the microneedle may extend from either of one of the two substrates, i.e., biosensor electrodes, wherein the microneedle and such associated electrode are integrated with each other.

Any suitable shape of skin-piercing element may be employed with the subject test strip devices, as long as the shape enables the skin to be pierced with minimal pain to the patient. For example, the skin-piercing element may have a substantially flat or planar configuration, or may be substantially cylindrical-like, wedge-like or triangular in shape such as a substantially flattened triangle-like configuration, blade-shaped, or have any other suitable shape. The cross-sectional shape of the skin-piercing element, or at least the portion of skin-piercing element that is penetrable into the skin, may be any suitable shape, including, but not limited to, substantially rectangular, oblong, square, oval, circular, diamond, triangular, star, etc. Additionally, the skin-piercing element may be tapered or may otherwise define a point or apex at its distal end. Such a configuration may take the form of an oblique angle at the tip or a pyramid or triangular shape or the like.

The dimensions of the skin-piercing element may vary depending on a variety of factors such as the type of physiological sample to be obtained, the desired penetration depth and the thickness of the skin layers of the particular patient being tested. Generally, the skin-piercing element is constructed to provide skin-piercing and fluid extraction functions and, thus, is designed to be sufficiently robust to withstand insertion into and withdrawal from the skin. Typically, to accomplish these goals, the ratio of the penetration length (defined by the distance between the base of the skin-piercing element and its distal tip) to diameter (where such diameter is measured at the base of the skin-piercing element) is from about 1 to 1, usually about 2 to 1, more usually about 5 to 1 or 10 to 1 and oftentimes 50 to 1.

The total length of the skin-piercing elements generally ranges from about 1 to 30,000 microns, usually from about 100 to 10,000 microns and more usually from about 1,000 to 3,000 microns. The penetration length of the skin-piercing elements generally ranges from about 1 to 5000 microns, usually about 100 to 3000 microns and more usually about 1000 to 2000 microns. The height or thickness of skin-piercing elements 6 and 86, at least the thickness of the distal portion of the skin-piercing element, typically ranges from about 1 to 1000 microns, usually from about 10 to 500 microns and more usually from about 50 to 250 microns. The outer diameter at the base generally ranges from about 1 to 2000 microns, usually about 300 to 1000 microns and more usually from about 500 to 1000 microns. In many embodiments, the outer diameter of the distal tip generally does not exceed about 100 microns and is generally less than about 20 microns and more typically less than about 1 micron. However, it will be appreciated by one of skill in the art that the outer diameter of the skin-piercing element may vary along its length or may be substantially constant.

Each of the skin-piercing elements of the test strip devices of FIGS. 1–4 has a space-defining configuration or structure therein which, upon insertion into the skin, creates a space or volume within the pierced tissue. This space serves as a reservoir within which bodily fluid is caused to pool in situ prior to being transferred to the biosensor portion of the subject test strip devices. Generally, the space-defining configurations of the present invention create or define a space within the pierced tissue having a volume at least as great as the available fluid volume in the reaction zone of the biosensor. Such pooling area volume ranges from about 10 to 1,000 nL, and more usually from about 50 to 250 nL. Such volume occupies a substantial portion of the entire volume occupied by the skin-piercing element, and ranges from about 50% to 99% and more usually from about 50% to 75% of the entire volume occupied by the skin piercing element.

Two exemplary configurations of the microneedle of the present invention are illustrated; however, such examples are not intended to be limiting. As illustrated in FIGS. 1 and 2, the microneedle's space-defining configuration is a recess 20 or 94 within a surface, e.g., the top surface, of skin-piercing structure 6 and 86. In many embodiments, recesses 20 and 94 have concave configurations wherein the depth of the recess is in the range from about 1 to 1000 microns and more usually from about 50 to 250 microns. Microneedles 6 and 86 may further be characterized by an opening 22 and 90, respectively, in the microneedle structure to further expose the pooling area defined by recess 22 and 86 to the outside environment, thereby increasing the volume and flow rate of body fluid into the pooling area.

Figure 3:
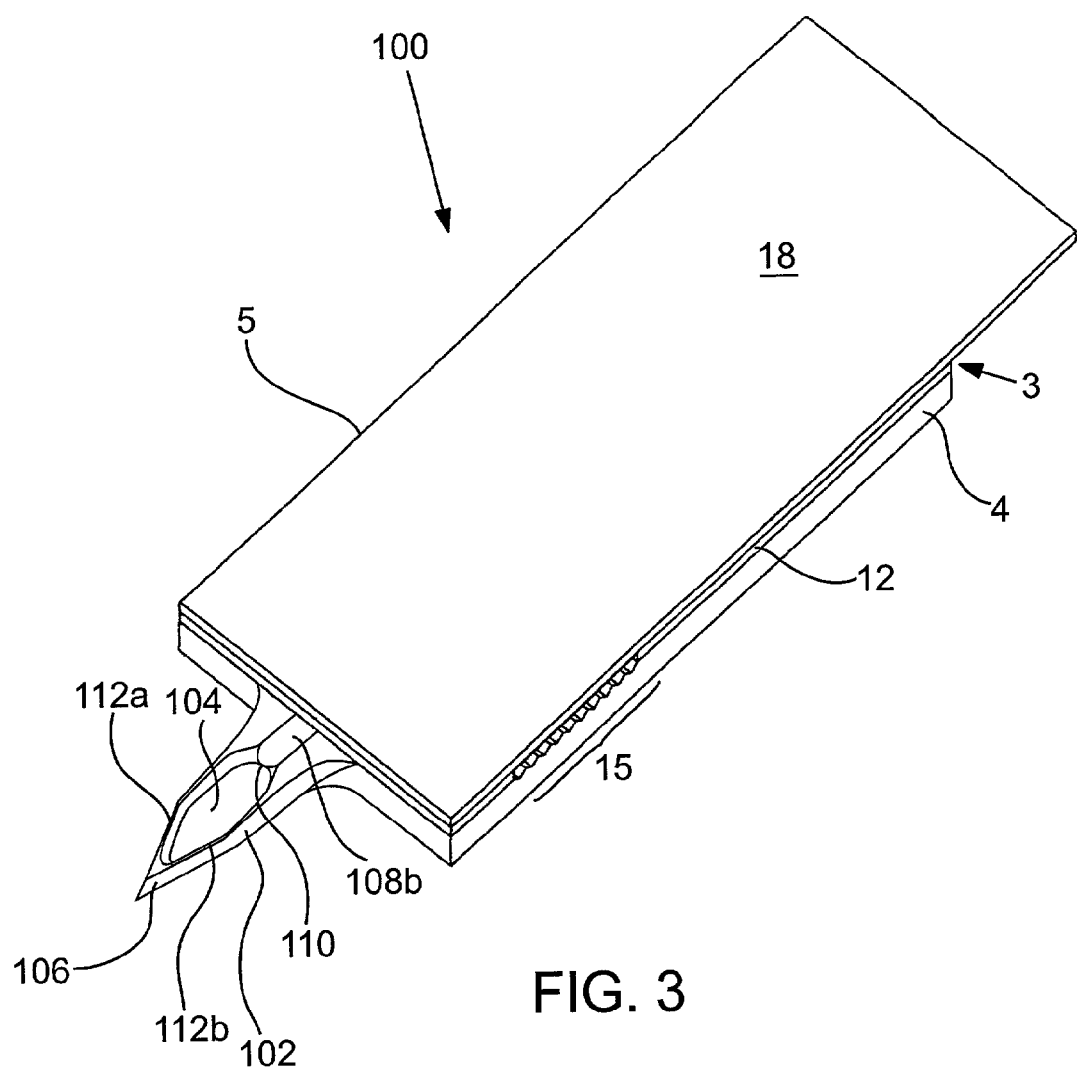
FIG. 3 is a perspective view of an electrochemical test strip device of the present invention having another embodiment of a skin-piercing element of the present invention.

In other embodiments, as illustrated in FIGS. 3 and 4, the space-defining configuration is an opening 104 and 124, respectively, which extends transverse to a dimension, e.g., width or thickness, of skin-piercing elements 102 and 122, respectively. In skin-piercing embodiments having more annular cross-sections, such opening transverses a diameter of the skin-piercing element. In the illustrated embodiments, openings 104 and 124 each occupy a substantial portion of the width of their respective skin-piercing elements 102 and 122, as well as a substantial portion of a length dimension of their respective test strips 100 and 120. Openings 104 and 124 define sidewalls 112*a* and 112*b* and sidewalls 132*a* and 132*b*, respectively, of microneedles 100 and 120, which have a thickness sufficient to maintain the structure of the microneedle when subject to normal forces.

The recesses 20 and 94 and openings 104 and 124 each define an open space or volume within the overall space or volume occupied by the respective skin-piercing element. Such space or volume creates a corresponding space or volume within skin tissue upon penetration into the skin, which acts as a sample fluid collection reservoir wherein fluid released upon penetration is pooled within the space. Such configuration is advantageous over conventional skin-piercing needles (i.e., a hollow needle or one having a closed outer surface defining an internal fluid transport lumen) which normally plug or close most of the pierced blood capillaries within skin upon penetration in such a way that body fluid cannot be extracted while the needle is still inserted within the skin. On the other hand, the open-spaced microneedle configurations and structures of the present invention create a free or open volume inside the skin which exposes a significant portion of blood capillaries pierced by the microneedle tip, referenced as 24, 92, 106 and 126 in FIGS. 1–4, respectively. As such, the availability of a greater volume of body fluid can be provided with a tip that is smaller and/or sharper than conventional microneedles, thereby reducing pain. The greater availability of body fluid also results in a faster collection rate of sampling.

Sample Fluid Extraction Channels and Sub-Channels

The subject test strip devices further include a sample fluid transfer or extraction pathway or channel, referenced as 10, 88, 108 and 128 in FIGS. 1, 2, 3 and 4, respectively, which extends from the open space of the respective microneedle to within the biosensor. At least a portion of the proximal end of the pathway resides within the biosensor portion of the test strip device. The distal end of the pathway may terminate just proximal to the microneedle structure (see FIGS. 2A and 2B) or may have a portion which resides within the skin-piercing structure (see FIGS. 1A, 1C, 3 and 4). In the latter configuration, such distal portion may be exposed to the outside environment.

In the test strip device of FIG. 1, bottom electrode 3 and microneedle 6 host a sample fluid transfer pathway or channel 10, wherein the proximal end 10*a* of pathway 10 resides within bottom electrode 3, specifically within reaction zone 9, and a portion of distal end 10*b* of pathway 10 resides within skin-piercing element or structure 6. Similarly, colorimetric test strip device 80 of FIG. 2, substrate 82 and skin-piercing element 86 host a fluid transfer pathway or channel 88, wherein the proximal end 88a of pathway 88 resides within substrate 82, specifically within matrix 84. However, unlike pathway 10, the distal end of pathway 88 terminates proximal to skin-piercing element 86. Test strip devices 100 and 120 of FIGS. 3 and 4, respectively, host fluid pathways 108 and 128, respectively, of which only the distal ends 108b and 128b are visible in the Figures. The distal ends 108b and 128b extend within a portion of microneedles 102 and 122, respectively, and their distal openings 110 and 130, respectively, terminate at associated openings 104 and 124.

The pathways or channels of the present invention are preferably dimensioned so as to exert a capillary force on fluid within the pooling area defined by the open space portion of the microneedle, and draws or wicks physiological sample to within the reaction zone or matrix area of the biosensor. As such, the diameter or width of a single fluid channel or pathway does not exceed 1000 microns and will usually be about 100 to 200 microns in diameter. This diameter may be constant along its length or may vary. In certain embodiments, the fluid pathway may further include one or more agents to facilitate sample collection. For example, one or more hydrophilic agents may be present in the fluid pathway, where such agents include, but are not limited to types of surface modifiers or surfactants such as MESA, Triton, Macol, Tetronic, Silwet, Zonyl and Pluronic.

As illustrated in the devices of FIGS. 1 and 2, channel 10 and 88, respectively, may further include one or a plurality of sub or side branches or sub-channels 15 and 96, respectively, which laterally extend from the proximal portion of the respective channel to within a portion or the entirety of the reaction zone 9 or matrix area 94. Such sub-channels 15 and 96 are created by forming ridges or ribs in the respective substrates 4 and 82, and/or the metal layer 3 which forms bottom electrode 3 of electrochemical test strip 2. These ridges could be formed during the microneedle microfabrication process. In test strip 2, electrode 5 acts as a cover over the ridges to form sub-channels 15. Similarly, in test strip 80, the matrix membrane or a clear film (not shown) acts as a cover over the ridges to form sub-channels 96. Sub-channels 15 and 96 each have diameters sufficient to provide a capillary force on fluid residing within channels 10 and 88, respectively. As such, the sub-channels facilitate the filling of reaction zone 9 and matrix area 84 with the sampled fluid. Sub-channels 15 and 96 have cross-sectional diameters in the range from about 1 to 200 microns and more usually from about 20 to 50 microns. In the illustrated embodiment, capillary branches 15 and 96 extend perpendicularly from channel 10 and 88, respectively; however, they may extend angularly from their respective channels.

Systems

Figure 5:
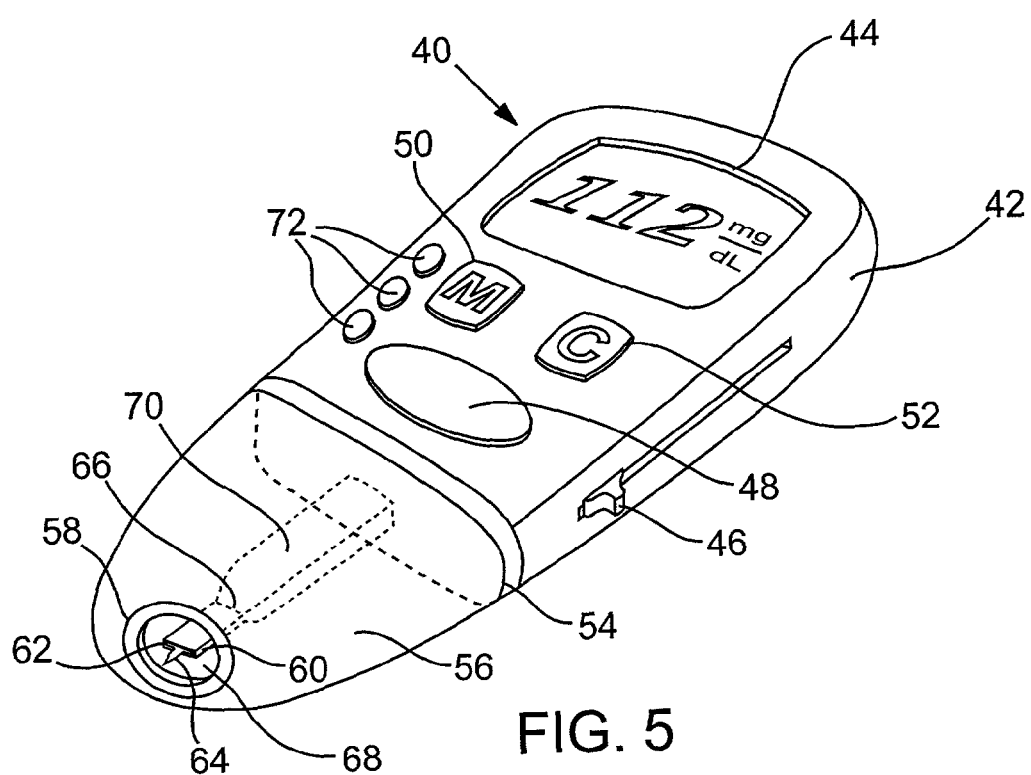
FIG. 5 illustrates a system of the present invention which includes a meter and a subject test strip device configured to be received by the meter.

As mentioned above, the subject devices may be used in the context of a subject system, which generally includes a system capable of obtaining a physiological sample and determining a property of the sample, where determining the property of interest may be accomplished automatically by an automated device, e.g., a meter. The subject system is more particularly described herein in the context of analyte concentration determination. Accordingly, as illustrated in FIG. 5, the analyte concentration determination system of the subject invention includes at least one test strip device 60 (having either an electrochemical or colorimetric configuration as described above) having at least one subject skin-piercing element 64, as described above, associated therewith, and a meter 40. The subject test strip devices, whether electrochemical or calorimetric, are configured and adapted to be inserted into meter 40. More specifically, as illustrated in FIG. 6, test strip device 60 has a first end 62 and a second end 66, wherein the skin-piercing element 64 is associated with first end 62 and at least the second end 66 is configured for insertion into a meter 40.

Meter 40 preferably has an ergonomically-designed housing 42 having dimensions which allow it to be comfortably held and manipulated with one hand. Housing 42 may be made of a metal, plastic or other suitable material, preferably one that is light weight but sufficiently durable. The distal portion 56 of housing 42 provides an aperture 68 through which test strip device 60 is translatable from a retracted position within meter 40 to an extended position wherein at least a portion of the test strip microneedle extends a distance distally from aperture 68. Distal portion 56 further defines a chamber in which test strip device 60 is received within a test strip receiving mechanism 70 of meter 40. Test strip device 60 may be inserted into meter 40 by removing distal housing portion 56 from housing 42 and inserting test strip device 60 into test strip receiving mechanism 70. Alternatively, test strip device 60 may be inserted into meter 40 and received into mechanism 70 via aperture 58. Preferably, distal housing portion 56 is transparent or semi-transparent to allow the user to visually confirm proper engagement between test strip device 60 and receiving area 70 prior to conducting the analyte concentration assay, as well as to visualize the test site and to visually confirm the filling of strip 60 with body fluid during the assay. When test strip device 60 is properly seated within receiving mechanism 70, the biosensor with test strip device 60 operatively engages with the meter's testing components. In other words, with electrochemical test strip embodiments, the electrodes of the biosensor operatively engage with the meter's electronics; and with colorimetric test strip embodiments, the matrix area having a signal producing system is operatively aligned with the meter's optical components. The meter's electronics or optical componentry, upon sensing when the reaction zone or matrix area, respectively, within test strip device 60 is filled with the sampled fluid, supplies an input signal to the test strip biosensor and receives an output signal therefrom which is representative of the sample fluid characteristic being measured.

Circumferentially positioned about aperture 68 is a pressure ring 58, the distal surface of which is applied to the skin and encircles the piercing site within the skin during a testing procedure. The compressive pressure exerted on the skin by pressure ring 58 facilitates the extraction of body fluids from the surrounding tissue and the transfer of such fluid into test strip device 60.

Distal housing portion 56 is itself in movable engagement with meter 40 wherein distal housing portion 56 is slightly translatable or depressible along the longitudinal axis of meter 40. Between distal housing portion 56 and the proximal portion of housing 42, is a pressure sensor 54 which senses and gauges the amount of pressure exerted on distal housing portion 56 when compressing pressure ring 58 against the skin. Pressure sensor 54 is an electrical type sensor which may be of the kind commonly known in the field of electronics. Pressure sensor indicators 72, in electrical communication with pressure sensor 54, are provided to indicate the level of pressure being applied to distal housing portion 56 so that the user may adjust the amount of pressure being applied, if necessary, in order to apply an optimal pressure.

In many embodiments, meter 40 has a display 44, such as an LCD display, for displaying data, such as input parameters and test results. Additionally, meter 40 has various controls and buttons for inputting data to the meter's processing components and for controlling the piercing action of test strip device 60. For example, lever 46 is used to retract test strip device 60 to a loaded position within meter 40 and thereby pre-load a spring mechanism (not shown) for later, on-demand extension or ejection of test strip device 60 from aperture 68 by means of depressing button 48. When distal housing portion 56 is properly positioned on the skin, such ejection of test strip device 60 causes microneedle 64 to instantaneously pierce the skin for accessing the body fluid therein. Buttons 50 and 52, when depressed, input signals to the meter's processing components indicating whether the measurement to be made is for testing/information purposes (and for recovering the test results from a memory means within the meter's electronics) or for calibration purposes, respectively.

Optionally, meter 40 may further be configured to receive and retain a replaceable cartridge containing a plurality of the subject test strip devices. After using a test strip device, meter 40 may either eject the used test strip from the meter or store them for disposal at a later time. Such a configuration eliminates the necessary handling of test strips, thereby minimizing the likelihood of damage to the strip and inadvertent injury to the patient. Furthermore, because manual handling of the test strips is eliminated, the test strips may be made much smaller thereby reducing the amount of materials required, providing a cost savings.

The meter disclosed in U.S. patent application Ser. No. 10/142,443, entitled "Minimal Procedure Analyte Test System," having attorney docket no. LIFE-054 and filed on the same day herewith, is of particular relevance and is suitable for use with the subject invention. Additionally, certain aspects of the functionality of meters suitable for use with the subject systems are disclosed in U.S. Pat. No. 6,193,873, as well as in copending, commonly owned U.S. application Ser. Nos. 09/497,304, 09/497,269, 09/736,788, 09/746,116 and 09/923, the disclosures of which are herein incorporated by reference. Of course, in those embodiments using a colorimetric assay system, a spectrophotometer or optical meter will be employed, where certain aspects of the functionality of such meters suitable for use are described in, for example, U.S. Pat. Nos. 4,734,360, 4,900,666, 4,935,346, 5,059,394, 5,304,468, 5,306,623, 5,418,142, 5,426,032, 5,515,170, 5,526,120, 5,563,042, 5,620,863, 5,753,429, 5,773,452, 5,780,304, 5,789,255, 5,843,691, 5,846,486, 5,968,836 and 5,972,294, the disclosures of which are herein incorporated by reference.

Methods

As summarized above, the subject invention provides methods for determining a characteristic of the sample, e.g., the concentration of an analyte in a sample. The subject methods find use in the determination of a variety of different analyte concentrations, where representative analytes include glucose, cholesterol, lactate, alcohol, and the like. In many embodiments, the subject methods are employed to determine the glucose concentration in a physiological sample.

While in principle the subject methods may be used to determine the concentration of an analyte in a variety of different physiological samples, such as urine, tears, saliva, and the like, they are particularly suited for use in determining the concentration of an analyte in blood or blood fractions, and more particularly in whole blood or interstitial fluid.

The subject methods will now be described in detail with reference to Figures. In practicing the subject methods, at least one subject test strip device as described above, is provided, and a subject microneedle 6 thereof is inserted into a target area of skin. Typically, the skin-piercing element is inserted into the skin of a finger or forearm for about 1 to 60 seconds, usually for about 1 to 15 seconds and more usually for about 1 to 5 seconds. Depending on the type of physiological sample to be obtained, the subject skin-piercing element 6 may be penetrated to various skin layers, including the dermis, epidermis and the stratum corneum, but in many embodiments will penetrate no farther than the subcutaneous layer of the skin.

While the subject test strips may be handled and inserted into the skin manually, the subject test strips are preferably used with the hand-held meter 40 of FIG. 5. As such, a test strip device 60 is either initially inserted into test strip receiving mechanism 70 either through aperture 68 or by temporarily removing distal portion 56 of housing 42 and placing the test strip into receiving mechanism 70 of meter 40. Alternatively, test strip device 60 may be provided pre-loaded within receiving mechanism 70. Still yet, as mentioned above, test strip device 60 may be collectively pre-loaded with a plurality of like test strips in a test strip cartridge (not shown). In such an embodiment, the cartridge is removably engageable with meter 40. Used strips may be automatically disposed of, e.g., either ejected from the meter or deposited into a separate compartment within the cartridge, while an unused test strip is automatically removed from the cartridge and inserted into receiving area 70 of meter 40.

Once test strip device 60 is properly received within mechanism 70, mechanism 70 may then be spring loaded or cocked by means of lever 46 of meter 40. As such, mechanism 70 and, thus test strip device 60, is in a retracted position. Meter 40 is then positioned substantially perpendicular to the targeted skin surface wherein distal housing portion 56, and more specifically pressure ring 58, is caused to contact the target skin area. Some compressive pressure may be manually applied to the target skin area, i.e., by pressing the distal end of meter 40 against the target skin area, to ensure that skin-piercing element 64 is properly inserted into the skin. By applying such pressure, a counter force causes distal housing portion 56 to press back upon pressure sensor 54 of meter 40. The relative amount (i.e., high, normal and low) of counter pressure is then measured and displayed by pressure sensor indicators 72. Preferably, the amount of pressure applied should generally be in the "normal" range. Indicators 72 inform the user as to when too much or too little pressure is being applied. When indicators 72 indicate that the applied pressure is "normal", the user may then depress the spring-release button 48. Due to the spring force released, receiving/carrying mechanism 70 and test strip device 60 are caused to thrust forward thereby causing skin-piercing element 65 to extend from aperture 68 and puncture the targeted skin area.

Whether by manual means or by use of meter 40, the penetration of skin-piercing element 64 into the skin creates a fluid sample pooling area (defined by the recess or opening within skin-piercing element) adjacent the fluid pathway, as described above, within element 64. Sample fluid enters the pooling area via the open-space configuration, e.g., recess or opening, within skin piercing element 64, and from the opposite side of skin-piercing element 46. The pooled sample fluid is then transferred via the fluid pathway by at least a capillary force exerted on the pooled fluid to the reaction zone or matrix within the biosensor of the test strip device 60. As mentioned above, the transfer of fluid may be further facilitated by exerting physical positive pressure circumferentially around the penetration site by means of a pressure ring 58 or by applying a source of negative pressure through the fluid channel thereby vacuuming the body fluid exposed to the distal end of the channel. The fluid entering the fluid pathway enters into the distal portion of the pathway first and then proceeds by capillary force (or by applied vacuum pressure) to within the proximal portion of the pathway which resides within the reaction zone or the matrix area. The fluid is then caused to translate laterally through the reaction zone or matrix area via sub-channels 15 or 96, respectively, wherein the entire available volume within the reaction zone or matrix area may be filled with the sample fluid.

Once meter 40 senses that the reaction zone or matrix area is completely filled with the sample of body fluid, the meter electronics or optics are activated to perform analysis of the extracted sample. At this point, the meter may be removed by the patient from the penetration site or kept on the skin surface until the test results are shown on the display. Meter 40 may alternatively or additionally include means for automatically retracting the microneedle strip from the skin once the reaction cell is filled with the body fluid sample.

When the biosensor reaction zone or matrix area is completely filled with the sample fluid, the concentration of the analyte of interest in the sampled fluid is determined. With an electrochemical based analyte concentration determination assay, an electrochemical measurement is made using counter/reference and working electrodes. The electrochemical measurement that is made may vary depending on the particular nature of the assay and the test strip with which the electrochemical test strip is employed, e.g., depending on whether the assay is coulometric, amperometric or potentiometric. Generally, the electrochemical measurement will measure charge (coulometric), current (amperometric) or potential (potentiometric), usually over a given period of time following sample introduction into the reaction area. Methods for making the above described electrochemical measurement are further described in U.S. Pat. Nos. 4,224,125; 4,545,382; and 5,266,179; as well as in International Patent Publications WO 97/18465 and WO 99/49307; the disclosures of which are herein incorporated by reference. Following detection of the electrochemical measurement or signal generated in the reaction zone as described above, the presence and/or concentration of the analyte present in the sample introduced into the reaction zone is then determined by relating the electrochemical signal to the amount of analyte in the sample.

For a colorimetric or photometric analyte concentration determination assay, sample applied to a subject test strip, more specifically to a reaction area of a test strip, is allowed to react with members of a signal producing system present in the reaction zone to produce a detectable product that is representative of the analyte of interest in an amount proportional to the initial amount of analyte present in the sample. The amount of detectable product, i.e., signal produced by the signal producing system, is then determined and related to the amount of analyte in the initial sample. With such colorimetric assays, optical-type meters are used to perform the above mentioned detection and relation steps. The above described reaction, detection and relating steps, as well as instruments for performing the same, are further described in U.S. Pat. Nos. 4,734,360; 4,900,666; 4,935, 346; 5,059,394; 5,304,468; 5,306,623; 5,418,142; 5,426, 032; 5,515,170; 5,526,120; 5,563,042; 5,620,863; 5,753, 429; 5,773,452; 5,780,304; 5,789,255; 5,843,691; 5,846, 486; 5,968,836 and 5,972,294; the disclosures of which are herein incorporated by reference. Examples of such colorimetric or photometric reagent test strips suitable for use with the subject invention include those described in U.S. Pat. Nos. 5,563,042; 5,753,452; 5,789,255; herein incorporated by reference.

Test Strip Device Fabrication Methods

As mentioned above, the skin-piercing elements of the present invention are preferably fabricated with a corresponding substrate (for colorimetric embodiments) or a substrate/electrode combination (for electrochemical embodiments), as a single, unitary piece or structure and made of the same material. Alternatively, the skin-piercing elements may be manufactured as separate components or pieces which are then affixed or attached to a corresponding substrate or substrate/conductive layer combination by any suitable means, for example, an adhesive commonly used in the art.

The test strip devices may be fabricated according to the present invention using any convenient techniques including, but not limited to, microreplication techniques including injection molding, photo-chemical etching (PCE), microstamping, embossing, and casting processes.

Because the test strip devices of the present invention are planar, the devices may be fabricated from and processed on one or more webs, films or sheets of suitable material. Such web-based manufacturing of the subject test strip devices provide significant cost advantage over more conventional methods in which test strips and the like are produced one at a time. FIGS. 6A–C and 7A–C illustrate such webs of fabricated test strip devices having electrochemical and photometric/colorimetric configurations, respectively.

While the following discussion of the subject fabrication methods is in the context of web-based manufacturing, the techniques discussed may also be used to make singular test strip devices. Additionally, while only certain fabrication techniques are emphasized, those skilled in the art will recognize that other known fabrication techniques may also be used which enable low cost manufacturing when desiring to form small structures having intricate features, such as the microneedles described above and the sample fluid channels and sub-channels within the reaction area of the subject test strip devices.

Fabrication of Electrochemical Test Strip Devices

Figure 6C:
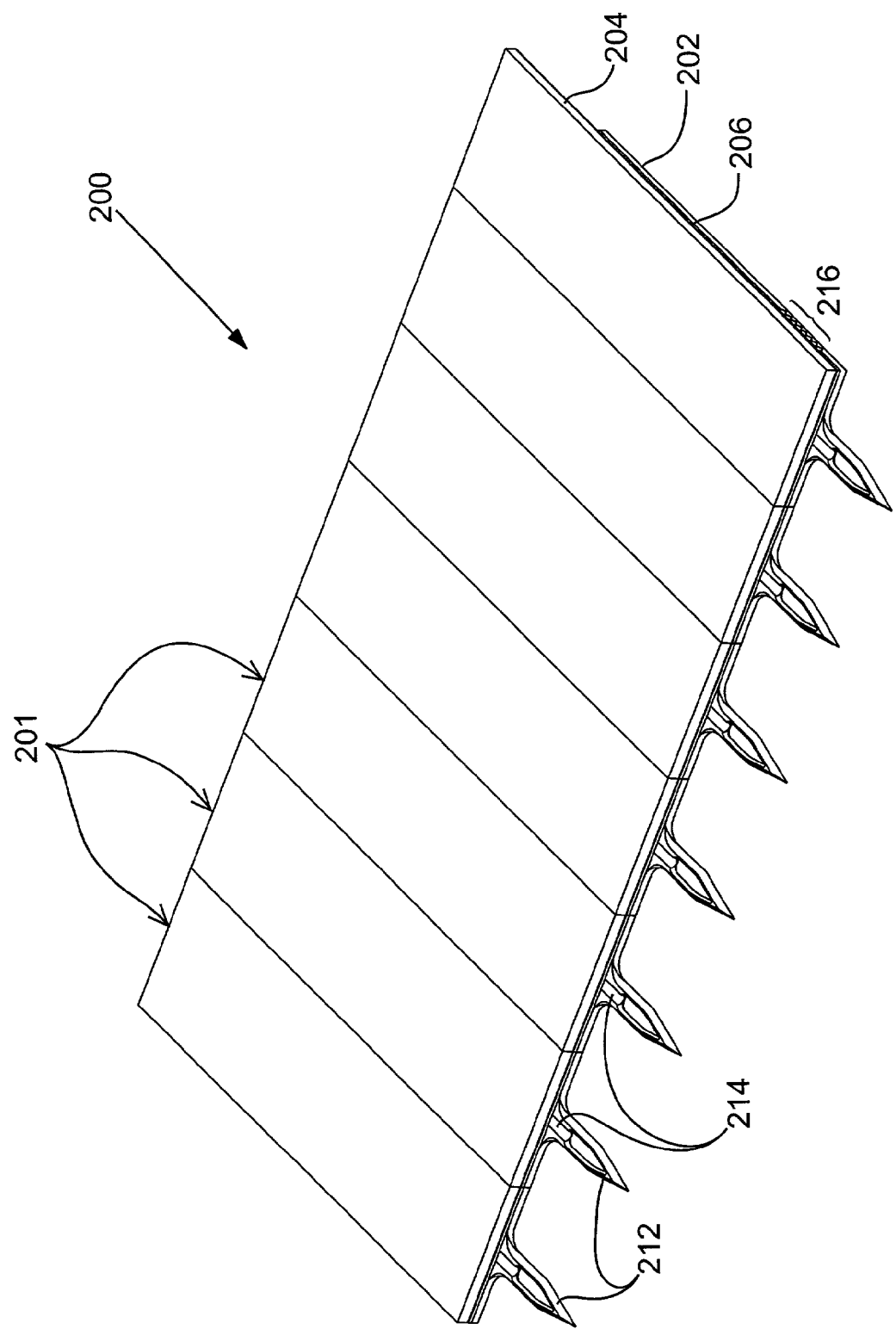
FIG. 6C is a perspective view of the assembled web of FIGS. 6A and 6B.

The electrochemical test strip device webbing 200 of FIGS. 6A–C includes a plurality of individual test strip devices 201 (shown fully assembled in FIG. 6C) fabricated in a side-to-side arrangement along the length of the webbing. Each test strip device 201 includes two spaced-apart electrodes, bottom electrode 202 and top electrode 204, and an insulating space layer 206 there between. Spacer layer 206 has a cut-out portion 208 which defines the reaction zone of the electrochemical biosensor containing a redox reagent system. A microneedle 212, shown having a configuration similar to that of microneedle 122 of FIGS. 4A and 4B, extends from and is planar with bottom electrode 202. Formed within a portion of bottom electrode 202 and a proximal portion of microneedle 212 is a channel 214 for transporting fluid pooled within the opening of microneedle 212. Extending laterally from both sides of channel 214 are a plurality of sub-channels 216 for facilitating the transfer and distribution of sampled fluid to within the reaction zone of the electrochemical biosensor.

Electrodes 202 and 204, as well as the associated microneedles, may be made entirely of metal or may be made up of an inert substrate or a support structure covered by a metal layer. Where the electrodes are primarily made of metal, photochemical etching (PCE) (also known as photochemical milling, chemical milling and photoetching) or microstamping techniques are suitable fabrication techniques.

With photochemical etching, suitable metals include, but are not limited to, aluminum, copper, gold, platinum, palladium, iridium, silver, titanium, tungsten, carbon and stainless steels. Fabrication may be done on sheets or continuous coils of metals. Such sheet provides a thin metal base for the etching process and generally has a thickness in the range from about 10 to 1,000 μm and more typically from about 50 to 150 μm. A photoresistant layer is then applied to one or both sides of the metal base as desired. Next, lithography techniques are used to precisely define the geometries that will be etched partially into, e.g., the fluid channels 214 and sub-channels 216, or etched completely through, e.g., the openings in the microneedles, the metal base. Specifically, the base metal is selectively masked to protect areas of the metal which are not to be etched and to expose areas of the metal which are to be etched.

Figure 8:
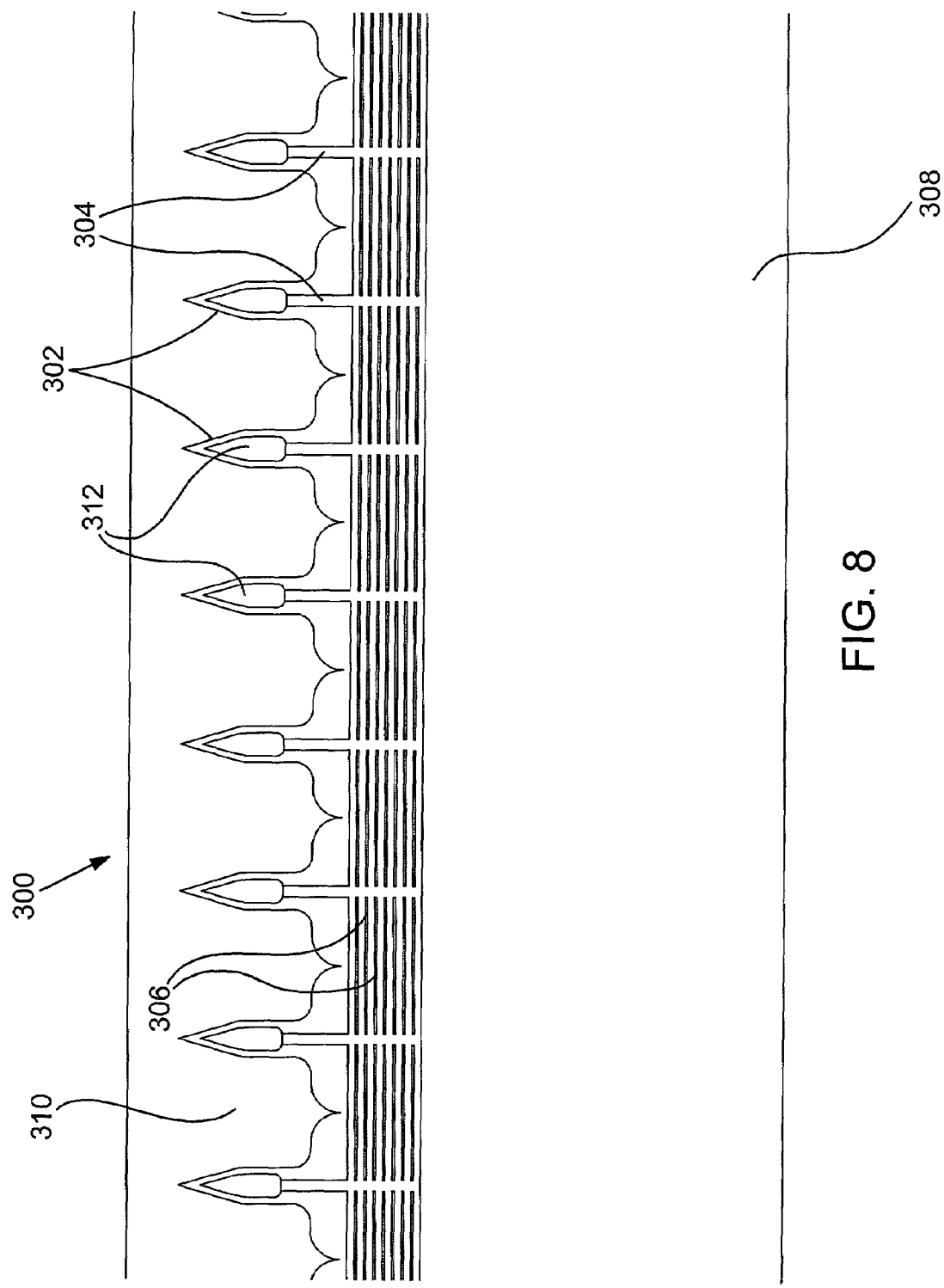
FIG. 8 is planar view of a web layer for use with the webs of FIGS. 6 and 7.

Etching is accomplished by an electrochemical dissolution process wherein an acid substance is applied to the surface of the base metal and a current is conducted through the metal. The areas of the metal surface which are not masked are then dissolved by the acid. After the etching step, the photoresist layer is stripped from the surface of the metal part, and, as illustrated in FIG. 8, the sheet 300 remains having a series of completely fabricated microneedles 302 and associated space-defining configurations 312, fluid transfer channels 304 and sub-channels 306. The portion 308 from which the bottoms substrates are to be cut, remains a continuous area of metal while the area 310 of sheet 300 has been cut etched away completely.

Microstamping, another technique suitable for fabricating all-metal electrodes or those made out of a very strong plastic material, involves the use of dies which have been precisely machined such as by electro-discharge machining (EDM). Long sheets or webbings of a substrate metal, such as those metals commonly used in PCE processing, are continuously or semi-continuously fed into a stamping press between die sets to selectively blank (i.e., punch holes in), coin (i.e., deform one side of the metal) and/or deform the metal substrate from both sides. This stamping process can performed at a rate of 1,200 strokes per minute and can produce multiple electrodes per stroke.

Where the electrodes 202 and 204 include an inert substrate material, hot embossing and injection molding techniques are suitable for fabrication of the subject devices particularly when the substrate material is a plastic. The substrate material is sufficiently rigid to provide structural support to the electrode and to the electrochemical test strip as a whole. Such suitable materials include polymers (plastics) and inorganic materials such as silicon, ceramic, glass, and the like. Suitable polymers include, for example, polyester, e.g., polyethylene terephthalate (PET), glycol modified polythelene terephthalate (PETG); polyimide, e.g., polyetherimide; polycarbonate; cellophane (regenerated cellulose); fluorinated polymer, e.g., polyvinyl fluoride, perfluoroalkoxy and fluorinated ethylene propylene copolymers; ionomer; polyamide, e.g., nylon 6, nylon 6,6, nylon 11, nylon 12; polyethylene and its copolymers; polystyrene and its copolymers; polypropylene and its copolymers; polymethylpentene; polyvinyl chloride and its copolymers; polysulfone; polyvinylidene chloride and its copolymers; and polymer composites reinforced with minerals or nanoparticles. A preferred material for the substrate is a Mylar plastic film.

With hot embossing, a precursor material such as a suitable thermoplastic precursor material having a thickness in the range of about 25 to 650 microns, usually from about 50 to 625 microns and more usually from about 75 to 600 microns is placed into an embossing apparatus, where such an apparatus includes a mold having features, often times a negative image of the features, of the skin-piercing element. The precursor material is then compressed by the mold under heat and a suitable compression force. Usually, a temperature in the range from about 20° C. to 1500° C. is used, usually from about 100° C. to 1000° C. and more usually from about 200° C. to 500° C. Heat is applied for about 0.1 to 1000 seconds, usually for about 0.1 to 100 seconds and more usually for about 0.1 to 10 seconds. The compression force is usually applied in the range from about 1 to 50 GPa is used, usually from about 10 to 40 GPa and more usually from about 20 to 30 GPa. The compression force is applied for about 0.1 to 100 seconds, usually for about 0.1 to 10 seconds and more usually for about 0.1 to 1 second. The heat and compression force may be applied at the same or different times. After the material is cooled, it is removed from the apparatus, and post processing may then occur.

Next, the upper side of the bottom substrate and the underside of the top substrate are metallized by vacuum sputtering or screen printing a conductive layer of metal over such substrates. The conductive layer may extend to cover the microneedle(s) 212 and, as such, the microneedle(s) functions as part of the associated electrode. More specifically, in certain electrochemical biosensor embodiments, the conductive material which is deposited over an inert substrate to form an electrode is also deposited over the sample fluid pathway or channel including the portion of the associated skin piercing element into which the fluid pathway extends. Suitable metals for the conductive layer include palladium, gold, platinum, silver, iridium, stainless steel and the like, or a metal oxide, such as indium doped tin oxide, or carbon, e.g., conductive carbon ink. In a preferred embodiment, the metal layer of electrode(s) 202 is gold and the metal layer electrode(s) 204 is palladium. An additional insulating layer may be printed on top of this conductive layer which exposes a precisely defined pattern of the electrode.

By means of any of the above fabrication techniques, bottom electrode(s) 202 functions as the counter/reference electrode and top electrode(s) 204 functions as the working electrode within the electrochemical cell. After fabrication of the electrodes, a redox reagent system is selected and deposited within the reaction zone 210 of bottom electrode(s) 202. Such deposition may be accomplished with slot coating, needle coating or ink jet printing techniques, which are well known in the art. The redox reagent system may also be deposited within the sample extraction channel. Optionally, the conductive surface of electrode 202 may be subsequently treated with a hydrophilic agent to facilitate transport of a fluid sample through the sample extraction channel and into the reaction zone 210. Suitable hydrophilic agent components include, for example, apoly(oxyethylene-co-oxypropylene) block polymer having the trade name Pluorinic™ F68, sodium dioctylsulfosuccinate having the trade name Aerosol™ OT 100%, octylphenoxypolyethoxy (9–10)ethanol having the trade name TRITON™ X-100, polyoxyethelene(20)sorbitan monolaurate having the trade name TWEEN™ 20, and polyoxyethelene(20)sorbitan monooleate having the trade name TWEEN™ 80, and 2-mercaptoethanesulfonic acid, sodium salt (MESA). In another embodiment redox reagent system may be deposited at the top electrode, i.e. layer 204 at the area corresponding to the zone 210 of the bottom layer 202 by the same deposition techniques. In yet another embodiment a redox system can be deposited on both electrodes, i.e., on layers 202 and 204 aligned so that the reagent coated chemistries face one another.

As mentioned above, electrodes 202 and 204 (and their respective webs) are separated by a spacer layer 206, or a web of such spacer layer, positioned or sandwiched between electrodes 102 and 104, or between their web structures. Spacer layer 106 may be fabricated from any convenient material, where representative suitable materials include polyethylene terephthalate, glycol modified (PETG), polyimide, polycarbonate, and the like. Both surfaces of spacer layer 106 have an adhesive to allow it to adhere to the respective electrodes. By process known in web-based manufacturing, all three layers are aligned in a stacked relationship and laminated together into assembled web 200 which is then cut into singulated test strip devices 201.

Fabrication of Photometric/Colorimetric Test Strip Devices

Many of the same techniques and processes, discussed above, for fabricating the electrochemical test strip devices of the present invention may also be used to fabricate the photometric/colorimetric test strip devices of the present invention.

Figure 7B:
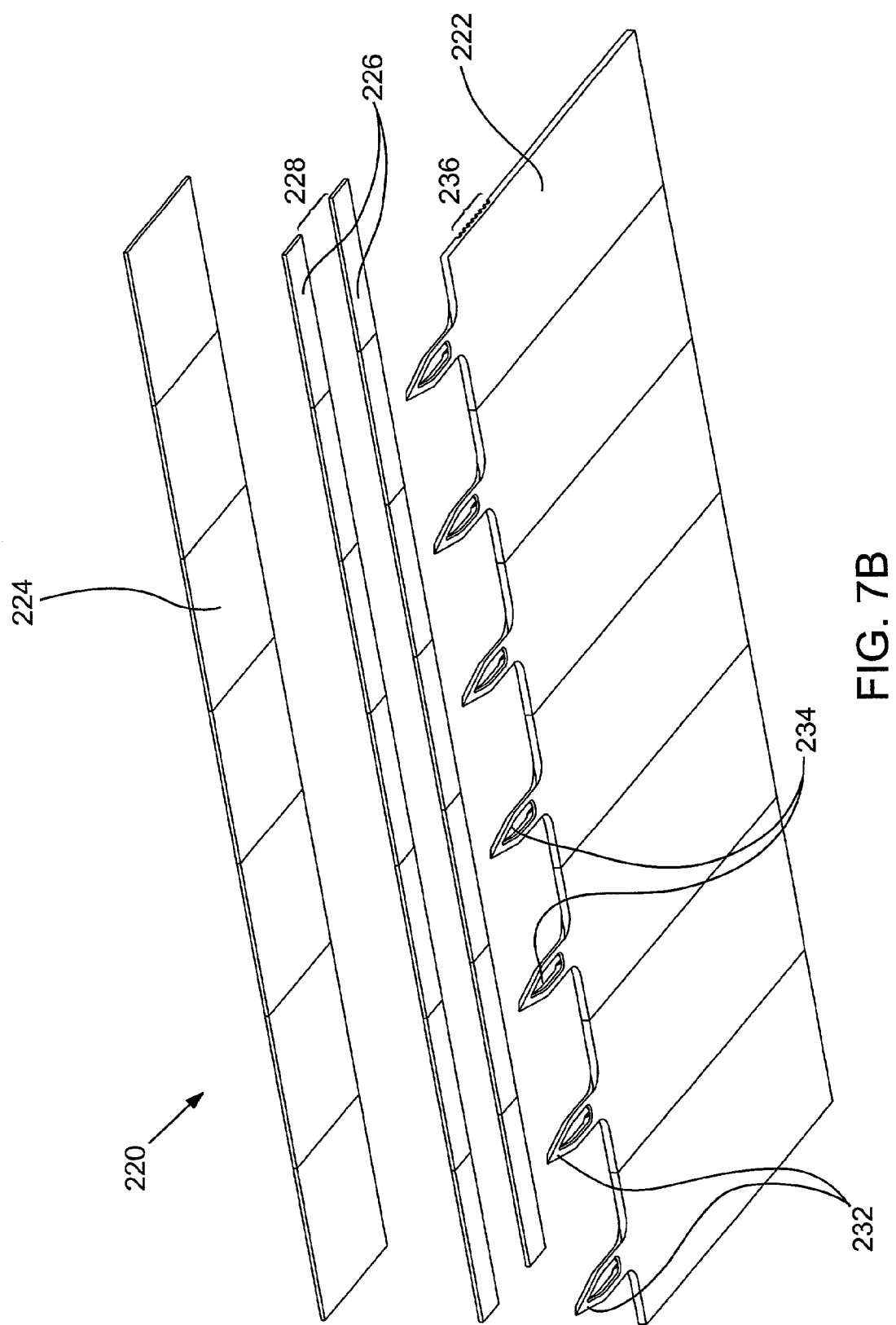
FIG. 7B is an exploded bottom view of the web of FIG. 7A.
Figure 7C:
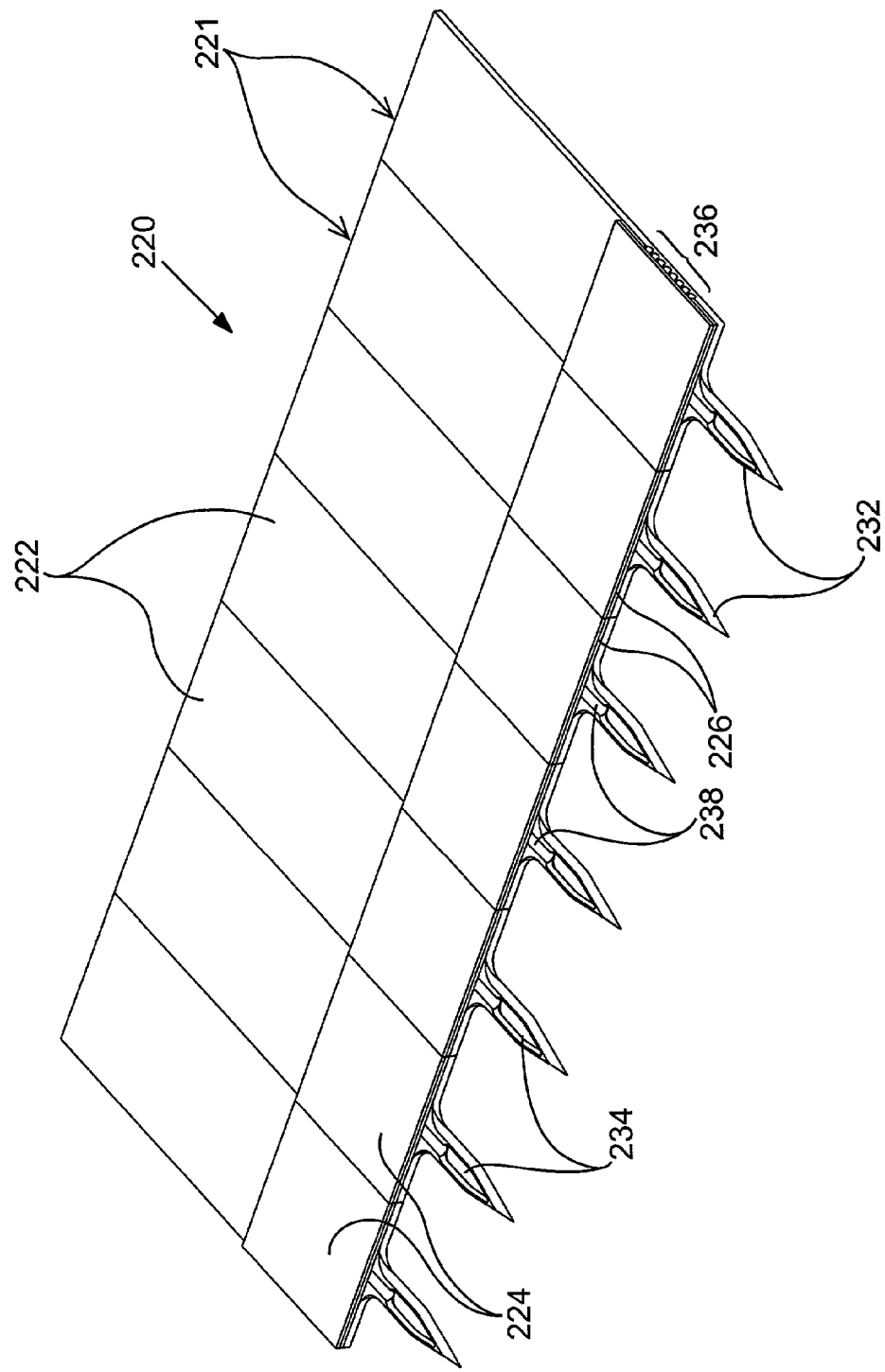
FIG. 7C is a perspective view of the assembled web of FIGS. 7A and 7B.

Referring now to FIGS. 7A–C, the fabrication of the photometric/colorimetric devices of the present invention is described. A webbing 220 (shown assembled in FIG. 7C) includes a plurality of individual test strip devices 221 fabricated in a side-to-side arrangement along the length of webbing 220. Such test strip devices 221 have a metal substrate configuration as described above with respect to FIGS. 4A and 4B. However, the subject fabrication techniques also apply to photometric test strip devices having inert material substrates as described above with respect to FIGS. 2A and 2B.

Webbing 220 is formed of at least three layers of sheets, a metal substrate sheet 222, a membrane sheet 224 and a double-sided adhesive layer 226 there between. Double-sided adhesive layer 226 has a cut-out portion 228 which aligns with the matrix area 230 of the photometric biosensor which contains a signal producing system. A plurality of microneedles 232, shown having a configuration similar to that of microneedle 122 of FIGS. 4A and 4B, extend from and are planar with substrate sheet 222. Formed within a portion of each substrate 222 and a proximal portion of microneedle 232 is a channel 238 for transporting fluid pooled within the opening 234 of each microneedle 232. Extending laterally from both sides of each channel 238 are a plurality of sub-channels 230 for facilitating the transfer and distribution of sampled fluid to within matrix 236 of the photometric biosensor.

As mentioned above, substrate sheet 222 as well as the associated microneedles 232 are made of metal, but may be made up of an inert material. Where the substrate made of metal, photochemical etching (PCE) and microstamping are suitable fabrication techniques. As with the electrochemical test strip devices, suitable metals for the substrate include, but are not limited to, aluminum, copper, gold, platinum, palladium, iridium, silver, titanium, tungsten, carbon and stainless steels. The metal sheet provides a thin metal base for the etching process and generally has a thickness in the range from about 10 to 1,000 µm and more typically from about 50 to 150 µm. A photoresistant layer is then applied to one or both sides of the metal base as desired. Next, lithography techniques are used to precisely define the geometries that will be etched partially into, e.g., the fluid channels 238 and sub-channels 230, or etched completely through, e.g., the openings 234 in the microneedles 232, the metal base. Specifically, the base metal is selectively masked to protect areas of the metal which are not to be etched and to expose areas of the metal which are to be etched. The electrochemical dissolution process of sheet 222 is as described above with respect to the electrochemical test strip devices of FIGS. 6A–6C, producing a sheet having the configuration of sheet 300 of FIG. 8.

Where the substrate sheet 222 is to be made of an inert substrate material, hot embossing and injection molding techniques, as described above with respect to fabrication of the electrochemical test strip devices, may be used for fabrication of the subject photometric test strip devices. The substrate material is sufficiently rigid to provide structural support to the electrode and to the electrochemical test strip as a whole. Such suitable inert materials for making support substrate sheet 222 include but are not limited to polyolefins, e.g., polyethylene or polypropylene, polystyrene or polyesters.

After fabrication of substrate 222, a signal producing system, as described above, is selected and deposited within matrix 230. Such deposition may be accomplished with slot coating, needle coating or ink jet printing techniques, which are well known in the art. The signal producing system may also be deposited within the sample extraction channels 238. Optionally, the surface of matrices 230 as well as channels 238 may be subsequently treated with a hydrophilic agent having a surfactant to facilitate transport of a fluid sample through the sample extraction channel 238 and into the matrix 230.

As mentioned above, substrate sheet 222 and membrane sheet 224 are separated by a double-sided adhesive layer 226. Double-sided adhesive layer 226 may be fabricated from any convenient material, where representative suitable materials include polyethylene terephthalate, glycol modified polyethylene terephthalate (PETG), polyimide, polycarbonate, and the like. Both surfaces of spacer layer 226 have an adhesive to allow it to adhere to substrate 222 and membrane sheet 224. In embodiments where substrate sheet 222 is made of an inert material, a spacer layer is not used. Instead, the side of membrane sheet 224 which is to contact substrate sheet 222 is provided with an adhesive coating, thereby allowing it to adhere to substrate sheet 222. By processes known in web-based manufacturing, all layers, i.e., two, three or more as the case may be, are aligned in a stacked relationship and laminated together into assembled web 230 which is then cut into singulated photometric test strip devices 221.

Kits

Also provided by the subject invention are kits for use in practicing the subject methods. The kits of the subject invention include at least one subject test strip device, oftentimes a plurality of test strip devices, where the at least one test strip device comprises at least on skin-piercing element. The kits may also include a reusable or disposable meter that may be used with disposable tests strip devices. When a plurality of test strip devices is provided, they may be collectively packaged within a cartridge, which may be reusable or disposable. Certain kits may include various types of test strip devices, e.g., electrochemical and/or colorimetric test strip devices. Such various test strip devices may contain the same or different reagents. Finally, the kits may further include instructions for using the subject test strip devices and meters in the determination of an analyte concentration in a physiological sample. These instructions may be present on one or more of the packaging, label inserts, containers in the kits, and the like.

It is evident from the above description and discussion that the above described invention provides a simple, quick, safe and convenient way to obtain a physiological sample and determine an analyte concentration thereof. The above described invention provides a number of advantages, including ease of use, decreased testing times, efficiency and minimal pain. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of fabricating at least one test strip device for collecting a sample of physiological fluid and measuring a characteristic thereof, said method comprising:
    integrally forming a substrate and at least one microneedle extending planar therefrom; and
    forming an opening within said at least one microneedle using photochemical etching techniques, wherein said opening occupies at least a portion of a width, diameter or length dimension of said microneedle, wherein the substrate acts as a first electrode and is overlaid with an insulation layer and a sheet of material forming a second electrode.

2. The method according to claim 1 wherein said substrate and said at least one microneedle comprise a metal material.

3. The method according to claim 2 wherein said metal material comprises one or more of the group consisting of aluminum, copper, gold, platinum, palladium, iridium, silver, titanium, tungsten, carbon and stainless steel.

4. The method according to claim 1 wherein said substrate and at least one microneedle comprise an inert material.

5. The method according to claim 2 wherein said substrate and at least one microneedle comprise an inert material.

6. The method according to claim 4 or 5 wherein said inert material comprises one or more of the group consisting of a polymer, silicon, ceramic and glass.

7. The method according to claim 6 wherein said polymer comprises one or more of the group consisting of polyester, polyimide, polycarbonate; cellophane, fluorinated polymer, ionomer, polyamide, polymethylpentene, polysulfone, polyethylene and its copolymers, polystyrene and its copolymers, polypropylene and its copolymers, polyvinyl chloride and its copolymers, polyvinylidene chloride and its copolymers, and polymer composites reinforced with minerals or nano-particles.

8. The method according to claim 1 wherein said step of forming an opening comprises forming a recess within a surface of said at least one microneedle.

9. The method according to claim 1 further comprising forming a fluid pathway extending from said recess to a location within said substrate.

10. The method according to claim 9 further comprising forming sub-channels extending from said fluid pathway within said test strip device.

11. The method according to claim 1 comprising using web-based fabrication techniques wherein said substrate and said at least one microneedle are formed from a web of suitable material.

12. A method of fabricating a plurality of test strip devices, said method comprising:
    providing a first sheet comprising a metal material and photochemically etching a plurality of skin-piercing elements within said first sheet wherein said plurality of skin-piercing elements extend from and are in the same plane as the said first sheet of material and the first sheet of material is configured to be used as a first electrode, wherein each of said skin-piercing elements comprises an opening occupying at least a portion of a width, diameter or length dimension of said respective skin-piercing element;
    providing a second sheet that is formed of an insulating material;
    laminating together said first and second sheets; and
    cutting said laminated sheets to provide said plurality of test strip devices.

13. The method of claim 12 wherein said first sheet is further made of an inert material.

14. The method of claim 13 wherein said metal material is deposited on said inert material.

15. The method of claim 12 wherein said first sheet further comprises an inert material.

16. The method of claim 12 wherein said second sheet is an inert material.

17. The method of claim 16 further comprising the step of providing a third sheet wherein said second sheet is sandwiched between said first and third sheets during said step of laminating.

18. The method of claim 17 wherein said third sheet is comprised of the same material as said first sheet.

19. The method of claim 16 wherein said second sheet has an adhesive on at least one side.

20. The method of claim 17 wherein said third sheet is porous.

21. The method of claim 12 wherein a redox reagent system is applied to said first sheet.

22. The method of claim 12 wherein a signal producing system is applied to said first sheet.

* * * * *